United States Patent [19]
Bender

[11] Patent Number: 6,117,335
[45] Date of Patent: Sep. 12, 2000

[54] DECONTAMINATION OF WATER BY PHOTOLYTIC OXIDATION/REDUCTION UTILIZING NEAR BLACKBODY RADIATION

[75] Inventor: Jim Bender, Foresthill, Calif.

[73] Assignee: New Star Lasers, Inc., Auburn, Calif.

[21] Appl. No.: 09/028,019

[22] Filed: Feb. 23, 1998

[51] Int. Cl.$^7$ .................................................. C02F 1/32
[52] U.S. Cl. .......................... 210/745; 210/748; 210/759; 210/908; 250/435; 422/24
[58] Field of Search ..................................... 210/740, 745, 210/758–760, 764, 748, 96.1, 103, 105, 143, 192, 198.1, 205, 908; 250/435, 436, 492.1; 422/24, 28, 105, 111, 186.3

[56] References Cited

U.S. PATENT DOCUMENTS

| | | | |
|---|---|---|---|
| 4,141,830 | 2/1979 | Last ........................................... | 210/63 |
| 4,179,616 | 12/1979 | Coviello et al. ......................... | 250/257 |

(List continued on next page.)

OTHER PUBLICATIONS

*Water Disinfection with Ultraviolet Light*, Aquafine Wedeco Environment Systems, Inc. brochure, 1996.
*Ultraviolet—UV Disinfection in Power Cogeneration*, Ultrapure Water, vol. 12, No. 5, Jul./Aug. 1995; and.
*Photolytic oxidation of contaminated water using a high–energy, pulsed ultra–violet flashlamp operating in the blackbody regime*, James B. Bender, 1997 OSA Symposium, UV Sources for Lithography, materials processing, and Biomedical Applications: 2", Oct. 1997.
Auburn Journal, "*Two chemists may have 'stumbled' onto MTBE solution*", Jan. 2, 1998, 1 page.
Associated Press, "*New way to purify water that has MTBE*", undated, 1 page.
Sacramento Bee, "*EPA asked to reject MTBE fuel additive*", Dec. 10, 1997, 2 pages.
SN&R, "*Trouble on Tap: What's in Sacramento's drinking water?*", Dec. 11, 1997, 3 pages.
Komex–H2O Science, University of Southern California, "*Literature Review of Technologies for Treatment of Methyl Tertiary Butyl Ether (MtBE) in Drinking Water*", Apr. 22, 1997.
World Wide Web publications, "*Chevron Gasoline Questions and Answers: Methyl Tertiary Butyl Ether (MTBE)*", 8 pages.
World Wide Web publications. "*Biodegradation of MTBE and Other Oxygenates*", kulpa3.html at www.nd.edu, 2 pages.

*Primary Examiner*—Peter A. Hruskoci
*Attorney, Agent, or Firm*—Ray K. Shahani, Esq.

[57] ABSTRACT

A reactor system for decontamination of water by photolytic oxidation utilizing near blackbody radiation, the system comprising (1) a reaction chamber defining an internal space with an inlet and an outlet; and (2) a broadband radiator for generating radiant energy with wavelengths between about 150 nm and about 3 $\mu$m, the broadband radiator disposed within the reaction chamber, such that a sufficient dosage of broadband radiation irradiates the contaminants and/or the oxidant within the internal space of the reaction chamber thereby causing photolytic oxidation of the contaminants by direct action of the radiation on the contaminants to break chemical bonds by sustaining a free radical chain reaction of oxidizing components, thus breaking down the contaminants by way of atomic abstraction of the components of the contaminants. In preferred embodiments, at least a portion of the radiant energy is generated in a pulsed mode, such as between about 1 and about 500 pulses per second. In preferred embodiments, the broadband radiator generates radiant energy at a rate of between about 1 kW and about 10 MW., and the resultant dosage rate of broadband radiation is between 1 joule/cm$^2$ and about 5000 joules/cm$^2$. In preferred embodiments, the radiant energy is produced by at least one gas filled flashlamp having a gas plasma temperature of between about 9,500° K. and about 20,000° K.

7 Claims, 11 Drawing Sheets

U.S. PATENT DOCUMENTS

| | | | |
|---|---|---|---|
| 4,230,571 | 10/1980 | Dadd | 210/760 |
| 4,273,660 | 6/1981 | Beitzel | 210/760 |
| 4,274,970 | 6/1981 | Beitzel | 210/748 |
| 4,400,270 | 8/1983 | Hillman | 210/103 |
| 4,437,999 | 3/1984 | Mayne | 210/748 |
| 4,595,498 | 6/1986 | Cohen et al. | 210/192 |
| 4,787,980 | 11/1988 | Ackermann et al. | 210/638 |
| 4,792,407 | 12/1988 | Zeff et al. | 210/748 |
| 4,836,929 | 6/1989 | Baumann et al. | 210/638 |
| 4,849,114 | 7/1989 | Zeff et al. | 210/747 |
| 4,849,115 | 7/1989 | Cole et al. | 210/748 |
| 4,910,438 | 3/1990 | Farnsworth | 315/307 |
| 4,913,827 | 4/1990 | Nebel | 210/748 |
| 5,124,051 | 6/1992 | Bircher et al. | 210/748 |
| 5,124,131 | 6/1992 | Wekhof | 422/186.3 |
| 5,130,031 | 7/1992 | Johnston | 210/748 |
| 5,144,146 | 9/1992 | Wekhof | 250/492.1 |
| 5,151,252 | 9/1992 | Mass | 422/186.3 |
| 5,170,091 | 12/1992 | Wekhof | 313/163 |
| 5,178,755 | 1/1993 | LaCrosse | 210/195.1 |
| 5,308,480 | 5/1994 | Hinson et al. | 210/195.1 |
| 5,330,661 | 7/1994 | Okuda et al. | 210/748 |
| 5,466,367 | 11/1995 | Coate et al. | 210/96.1 |
| 5,480,562 | 1/1996 | Lemelson | 210/745 |
| 5,489,442 | 2/1996 | Dunn et al. | 426/248 |
| 5,547,590 | 8/1996 | Szabo | 210/748 |
| 5,648,592 | 7/1997 | Pierce | 588/227 |
| 5,658,530 | 8/1997 | Dunn | 422/24 |
| 5,768,853 | 6/1998 | Bushnell et al. | 53/167 |
| 5,786,598 | 7/1998 | Clark et al. | 250/455.11 |
| 5,789,755 | 8/1998 | Bender | 250/492.1 |
| 5,900,211 | 5/1999 | Dunn et al. | 422/24 |

DECONTAMINATION OF WATER BY PHOTOLYTIC OXIDATION/REDUCTION UTILIZING NEAR BLACKBODY RADIATION

FIELD OF THE INVENTION

The present invention relates to decontamination of water, and more particularly to methods and apparatus for decontamination of groundwater, surface water or waste water through the use of a highly efficient flashlamp or other source of high peak power, high average power, broadband, continuum output UV-rich radiation for rapidly and efficiently reducing or oxidizing (redox-ing) contaminants, including organic and inorganic molecules and for microbial sterilization of groundwater, surface water or waste water.

BACKGROUND OF THE INVENTION

Abundant quantities of clean, fresh water have long been available in the United States. The unfortunate introduction of pesticides, pathogens, and highly volatile gasoline components, such as MTBE, into the aquifers of many drinking water systems is now a serious constraint to economic expansion in developed countries, and a matter of survival for 20% of the world's population. As an example, the U.S. Environmental Protection Agency announced Nov. $26^{th}$, 1997, that it will be issuing a new health advisory citing cancer data and drinking water contamination relating to MTBE, and will recommend maximum levels of 20–40 parts per billion in drinking water. There exists a need for cost effective method to reduce MTBE levels to meet these standards.

Current water purification technologies, including distillation, reverse osmosis, and carbon filtration usually produce suitable water quality, but their high capital, operating and maintenance costs have limited their use to only those situations where water shortages are most extreme or where cost is less important. Water contaminated with pesticide or gasoline contaminants are especially difficult and costly to remove with conventional technologies.

The $5.5 billion annual worldwide water purification market is growing, depending on market segment between 5% and 25% per year. Thirty-three percent (33% or $1.8 billion) is for purification of fresh water for commercial, industrial and residential use. Waste water reclamation and re-purification, currently about $1.0 billion annually, is the fastest growing segment. The overall market demand is currently constrained by the high cost of water purification products. Availability of low-cost alternatives could cause the market to reach $18 billion by the year 2002.

Both advantages and disadvantages of the prior art technologies are summarized below:

Vapor compression (VC), including distillation technology systems are positive on drinking water for both pathogen and chemical contamination remediation, remove total dissolved solids (TDS) and are excellent for desalinization. Drawbacks include a relatively high price, a generally large size, non portability and fairly complex construction and operation.

Reverse osmosis (RO) removes TDS with a relatively simple mechanism. Removal of non-volatile organics, pathogens is easy. However, the systems are subject to contaminating product water if feed water pressure and turbidity are out of operating parameters, involve a high price rate, does not remove dissolved organic compounds and are complex and sophisticated.

Air stripping (AS) is generally the least expensive form of water remediation and is fairly good at removing volatile organics. However, these systems are also large, very noisy and unsightly, do not remove non-volatile organics, do not remove pesticides or pathogens, depend on ancillary technology, like the use of granulated activated carbon (below), resulting in more O&M cost as well as air pollution (the volatile organics are transferred into the atmosphere).

Granulated activated carbon (GAC) acts positively on volatile and non-volatile organics like pesticides, is positive on pathogens, and can be reactivated in most cases. However, GAC also requires re-supply of heavy, bulky material, typically has a large adsorption ratio, such as about 1000 pounds GAC to 1 pound contaminant, and itself becomes a source of contamination of product water if allowed to saturate. Furthermore, saturated GAC is a hazardous waste product and must be handled as such, especially when considering issued including transportation, disposal or reactivation cost.

Low and medium pressure mercury vapor ultraviolet (UV) radiation is also effective at destroying pathogens, but only very slightly positive on organic or synthetic organic compounds at practical flow rates. Sometimes UV is used as part of a polishing loop on larger treatment systems. However, as a practical matter, use of UV radiation in the past has been impossible. These systems are not practical for chemically contaminated water, the required low pressure lamps are typically not self cleaning, would require hundreds of lamps to equal the dosage of a lamp of the present invention, and provide a larger footprint for any type of remediation application.

Ozone saturation is positive on pathogens and leaves no dangerous chemicals in the water. However, providing a system which injects ozone into a water supply or stream typically requires a physically rather large footprint and is complex to build and operate, involves high operation and maintenance costs, involves the production of ozone—a dangerous and reactive gas, and is not practical on chemical contaminants alone.

Finally, the use of chlorine (Cl) is known to render pathogens harmless pathogens but has no remedial effect on chemical contaminated water except for elimination of cyanides. Current competing technologies for chemical contamination of groundwater include reverse osmosis (RO), air stripping, and Activated Carbon filtration. Although the popularity of reverse osmosis has gained substantially in market share in recent years, different technology solutions continue to dominate the various niches. RO membrane production is dominated by a few companies (DuPont, Dow-Filmtec, Fluid Systems, Toyoba, etc.), but there are thousands of companies that act as integrators of RO systems. Few, with the notable exception of Ionics, Osmonics, and U.S. Filter exceed $100 million in revenues. Air stripping is less complicated and has low associated costs but is noisy, unsightly, pollutes the air, and has limited effectiveness in removing MTBE to EPA standard levels. Activated Carbon Filtration involves large quantities of carbon supplied by companies like Calgon, Inc.

Pathogen removal is accomplished with the addition of chlorine, distillation techniques, or the use of banks of low or medium pressure ultraviolet lamps. Distillation suppliers include large European, Japanese, and Korean contractors and this technology excels at the removal of TDS (total dissolved solids). Current ultraviolet lamp suppliers include Aquafine, Fisher & Porter, and Puress, Inc. There exists a need for technology which is more energy efficient and can simultaneously remove pathogens and chemical contamination. Such equipment could also be used to post-treat water at desalination facilities to remove chemical contaminants.

Traditional UV technology relies on low and medium pressure UV lamps, similar to the fluorescent lamps used in office buildings. Medium pressure lamps operate at higher power levels than do the low-pressure lamps and, consequently, are slightly more efficient than the standard low-pressure variety. The typical low-pressure power ranges from 30 to 100 watts while the medium pressures average 3000 watts. Both lamp types are known as atomic line radiators. They produce light energy in very narrow wavelength bands at 10–20% electrical efficiency. Both types operate with A/C current and are controlled by electrical ballast.

Though the lamp life is generally very long, maintenance cost are generally very high, especially in the case of low-pressure lamps. Cleaning is the main problem. Lamps become fouled in the water environment from precipitated dissolved solids and scum. This fouling action gradually reduces the UV output making the lamp useless. Therefore, these lamps must be removed on periodic bases and manually cleaned. Further more, low and medium pressure lamps do not produce the radiative power levels to effectively dissociate the chemical bonds of contaminants. They find their principle usage in the wastewater reclamation industry for biological degradation. At a single installation, these lamps are used hundreds and sometimes thousands at a time, thus amplifying the O&M cost.

Improvements to this type of technology include enhanced chemical doping of the lamp to increase its UV conversion efficiency, improved cold cathodes to increase lamp life and improved reaction chambers or effluent channels to maximize dosage and throughput and to minimize head loss.

The following U.S. patents are deemed relevant to the field of the present invention:

| Patent No. | Issue Date | Inventor |
| --- | --- | --- |
| 4,141,830 | Feb. 27, 1979 | Last |
| 4,179,616 | Dec. 18, 1979 | Coviello et al. |
| 4,230,571 | Oct. 28, 1980 | Dadd |
| 4,273,660 | Jun. 16, 1981 | Beitzel |
| 4,274,970 | Jun. 23, 1981 | Beitzel |
| 4,437,999 | Mar. 20, 1984 | Mayne |
| 4,595,498 | Jun. 17, 1986 | Cohen et al. |
| 4,787,980 | Nov. 29, 1988 | Ackermann et al. |
| 4,792,407 | Dec. 20, 1988 | Zeff et al. |
| 4,836,929 | Jun. 6, 1989 | Baumann et al. |
| 4,849,114 | Jul. 18, 1989 | Zeff et al. |
| 4,849,115 | Jul. 18, 1989 | Cole et al. |
| 4,913,827 | Apr. 3, 1990 | Nebel |
| 4,124,051 | Jun. 23, 1992 | Bircher et al. |
| 5,130,031 | Jul. 14, 1992 | Johnston |
| 5,151,252 | Sep. 29, 1992 | Mass |
| 5,178,755 | Jan. 12, 1993 | LaCrosse |
| 5,308,480 | May 3, 1994 | Hinson et al. |
| 5,466,367 | Nov. 14, 1995 | Coate et al. |
| 5,330,661 | Jul. 19, 1994 | Okuda et al. |
| 5,547,590 | Aug. 20, 1996 | Szabo |

Last teaches an apparatus for purifying liquid such as water, in which as ultraviolet light source irradiates air passing through a first chamber surrounding the source, and then irradiates the liquid passing through the second chamber surrounding the first chamber. The air from the first chamber is ozonated by the UV light, and this air is bubbled into the water in the second chamber to maximize the purification through simultaneous ultraviolet and ozone exposure.

Beitzel teaches water treatment by passing a mixture of water and air and/or ozone through a nozzle which compresses and breaks up bubbles within the fluid mixture in a radiation housing, a hollow, cylindrical chamber located around an elongated UV light source. Beitzel also teaches water treatment by passing a thin film of water in contact with a bubble of air containing air and ozone while concurrently radiating both the water film and the air/ozone bubble with UV radiation.

Mayne teaches a method of feeding an insoluble organic solid material n the form of an organic resin or biological matter containing contaminating material such as radioactive waste from a nuclear facility or from treatment of animal or plant tissue in a laboratory or medical facility into a vessel containing water and, to which ultraviolet light and ozone, preferably by sparging, are applied.

Cohen et al. teaches a water purification system which includes an ion-exchange unit for producing high-resistivity water, followed by ozone exposure and ultraviolet sterilizer units that oxidize organics and also reduce resistivity, followed by a vacuum degassification unit to restore high resistivity.

Ackermann et al. is directed to a hydraulic multiplex unit for receiving continuously one or more samples of liquid from a liquid purification system distribution system and redirecting such sample or samples randomly or in sequence to one or more analytical instruments.

Zeff et al. teaches a method of oxidizing organic compounds in aqueous solutions by using in combination ozone, hydrogen peroxide and ultraviolet radiation. Zeff et al. also teaches a method of oxidizing toxic compounds including halogenated and/or partially oxygenated hydrocarbons and hydrazine and hydrazine derivatives in aqueous solutions by using in combination ozone, hydrogen peroxide and ultraviolet radiation.

Baumann et al. teaches a process for breaking down organic substances and/or microbes in pretreated feed water for high-purity recirculation systems using ozone which is generated in the anode space of an electrochemical cell and treated with ultraviolet rays and/or with hydrogen ($H_2$) generated in the cathode space of the same cell or hydrogen ($H_2$) supplied from outside, for use in reducing elementary oxygen in any form to harmless water.

Cole et al. teaches a process and apparatus for oxidizing organic residues in an aqueous stream, comprising a chamber with an inlet and an outlet and dividers therebetween creating subchambers, each subchamber having a source of ultraviolet light disposed therein, and means for controlling flow including flow through subchambers and means for controlling radiation to the fluid, such as when the subchambers are closed and flow is interrupted, and not when the subchambers are open such as during periods of flow it thereinto or therefrom.

Nebel teaches a method for producing highly purified pyrogen-free water comprising dissolving ozone in water, separating the gas and liquid phases, and exposing the ozone-containing water to ultraviolet radiation to destroy pyrogen in the water.

Bircher et al. teaches a process for treating aqueous waste or groundwater contaminated with nitro-containing organic chemicals to degrade the compound sufficiently to permit disposal of the waste or groundwater.

Johnston teaches a process for removing halogenated organic compounds from contaminated aqueous liquids which comprises contacting the contaminated liquid with a photocatalyst while simultaneously exposing the contaminated liquid to both acoustic energy and light energy to efficiently decompose the halogenated organic compounds.

Mass teaches a reactor for the treatment of a fluid with a substantially uniform dosage of light from a line-type light source, and not a blackbody radiator, in a reactor housing with a central photochemical treatment region.

LaCrosse teaches an ultraviolet-enhanced ozone wastewater treatment system in which ozonated water is mixed within a multi-stage clarifier system with wastewater to be treated and suspended solids are removed. The clarified effluent is filtered and exposed to ultraviolet radiation. Ozone is injected into a contact tower, where reaction takes place, and the UV irradiated, ozonated and clarified liquid is recirculated through an ozone injector and discharged through a mixer plate into a purge chamber, from where a portion is re-diverted to the system and a portion is discharged through a diverter valve through a carbon filter and out the system.

Hinson et al. teaches a two-stage, multiphase apparatus for the purification of water which may contain solid wastes. Gaseous oxidant comprising ozone and oxygen initially removes the solids, and then resaturation with oxidant breaks down and destroys chemical and biological contaminants, prior to UV radiation, degassification and rejection from the system.

Coate et al. teaches a portable system which minimizes the addition of solids to be disposed of through the use of ozone for contaminant reduction to basic elements after the pH value of the waste water to be treated is properly adjusted. Ozone is combined with ultrasound to cause coagulation and precipitation. In another stage, ozone and UV light are used in a reduction process. Ion alignment using a magnetic field and an electrochemical flocculation process to which the waste water is subjected causes further coagulation and precipitation.

Okuda et al. teaches decomposition of an organochlorine solvent contained in water by adding at least one of hydrogen peroxide and ozone to the water and then radiating ultraviolet rays to the water. A catalytic amount of a water-insoluble barium titanate substance is caused to co-exist in the water.

Szabo teaches a UV based water decontamination system with dimmer-control, in which a UV based or dual mode water system operates under household water pressure to provide a batch treatment of contaminated water. Treated water is stored in a pressurized reservoir from which it may be released for use. A pressure drop, or discharge of a sufficient amount of the treated water initiates another treatment cycle. A pressure gauge linked to a UV lamp dimmer detects the pressure drop and causes the UV lamp output to change from a reduced-output, standby mode to an operative mode. lamp output is also linked to filter backwash. The UV light may also be used to produce ozone which is placed in contact with the fluid through a helical tube.

OBJECTS AND ADVANTAGES OF THE PRESENT INVENTION

Thus, it is an object and an advantage of the present invention to provide a system which requires a drastically reduced operating footprint. It would be desirable to provide one lamp which can provide the same dosage that would take hundreds of mercury UV lamps and can do so more efficiently in that most of the lamp's blackbody radiation spectrum is used (80%). In contrast, the mercury lamps of the prior art use a very narrow band of UV energy with an energy efficiency of 15–20%.

Another object and advantage of the present invention is to provide UV blackbody radiation that ranges from about 0.75 million to about 9 million watts of ultra-violet power (~50% of peak power generated) at average powers ranging from about 2,500 watts to about 18,750 watts per lamp. These power levels would easily provide enough energy per pulse to dissociate chemical bonds and a sufficient number of pulses per second will sustain the free radical chain reaction necessary to oxidize/reduce the contaminants.

Another object and advantage of the present invention is to provide thousands of times more dosage to destroy pathogens, at a lower energy cost, than the standard, currently marketed, UV technology.

Another object and advantage of the present invention is to provide a unique reaction chamber design which overcomes the problems of light absorption based on water quality. In this way, water that has a high level of dissolved solids, that would normally absorb little light energy, can be used without any extra filtering or pretreatment.

Another object and advantage of the present invention is to provide equipment which can be produced in volume and inexpensively, resulting in lower capital cost per unit. Another object and advantage of the present invention is to provide a system having low operating and maintenance costs. Such systems would operate automatically with minimal maintenance.

Another object and advantage of the present invention is to generate longer wavelength blackbody radiation having typical power output rates ranging from about 0.45 million to about 2.7 million watts (~30% of the energy generated).

Another object and advantage of the present invention is to provide high intensity broadband radiation to provide the absorption wavelengths necessary for disruption of essentially and effectively all organic bonds, resulting in high efficiency organic bond dissociation, with as much as or more than 80% of the total light energy generated used to oxidize the constituent contaminants.

SUMMARY OF THE INVENTION

This invention is based on the ability of a high-energy flashlamp to photodegrade chemical contaminants in water. By adjusting the input energy, pulse duration, and pulse shape waveform of the energy applied to the flashlamp, blackbody radiation, which peaks in the deep UV, is attainable. The ionization of the plasma within the flashlamp is predominately caused by free-bound and bremsstrahlung continuum transitions in which the bound-bound line transitions are superimposed. The plasma, being mostly continuum in nature, yields a high emissivity ($0.98 < \epsilon < 1$) across the UV-VIS-IR bands.

Significant differences between the lamps used in the present invention and traditional UV lamps are that (1) the present UV lamps have no phosphor coating which would otherwise primarily serve to convert any UV energy into visible light, and (2) the lamp envelope is made from quartz ($SiO_2 \geq$ app.98%), which allows the UV energy to pass through, and not glass.

A multi-pass reaction chamber design couples the high-energy light pulse to the contaminated water. Each reaction chamber, containing one lamp, takes advantage of the 360-degree circumferential radial radiation pattern of the lamp. The reaction chamber also takes advantage of the non-Lambertian volume-emitter radiation profile of the lamp, at least to the extent of the quartz-water total internal reflectance (TIR). At 185 nm, the light intensity degrades by only 4% at 40° from lamp normal. In a Lambertian source, the intensity falls to 15% of maximum.

Since the system is modular, extending the reaction chambers in a parallel or series fashion provides more reaction area and exposure time to accommodate higher flow rates and contaminant concentrations. However, for more efficient oxidation, a method of adjusting the oxygen concentration, Total Dissolved Solids (TDS) and turbidity of the water to optimal levels should be used before the water reaches the reaction chamber.

The process can clean groundwater, surface water, and wastewater of toxic chemicals and dangerous pathogens quickly and inexpensively. Chemical contaminants are redox-ed into smaller, less complex molecules and are finally redox-ed into safer compounds such as $CO_2$, $H_2O$, and low level organic acids, which pose no health or aesthetic threat to drinking water. In super high concentrations, the contaminant concentration is drastically reduced to safe levels, as established by the EPA. In the case of pathogens, the DNA/RNA of the bacteria or virus are destroyed instantly by the intense UV energy. This level of destruction prevents the pathogens from reproducing.

Unlike other forms of water remediation, the pulsed flashlamp photolytic redox technology is small, compact, and environmentally friendly. Because the system does not generate loud or obnoxious sounds and is not unsightly, it can be placed in quiet neighborhoods, business districts, and "environmentally sensitive" areas such as national parks or other scenic areas.

A significant advantage of the present invention is increased UV flux. With the present system, just one lamp can generate up to 10 megawatts of UV radiation having wavelengths ranging continuously between about 185 nm and about 400 nm in a single pulse lasting only a fraction of a second. These pulses can be applied at a rate of about 5 to about 100 pulses per second resulting in ultraviolet dosages ranging from about 50 joules/cm$^2$ to about 2000 joules/cm$^2$. One lamp provides about 50 to about 550 times the UV dosage as compared to current low and medium pressure lamp based technology that uses hundreds of lamps to achieve similar dosages.

It should be pointed out that the low and medium pressure mercury UV lamps only radiate at a few narrow wavelengths in the UV, due to atomic line radiation, namely: 185 nm (on special lamps), 254 nm, and 365 nm. There are sometimes other wavelengths present but their energy levels are so low as not to matter in a practical application.

On the other hand, the lamps of the present invention radiate in the ultraviolet essentially continuous between about 185 nm and about 400 nm, encompassing all the wavelengths in between in a blackbody radiation profile (continuum radiation). The present lamps also radiate in the visible and infrared from between about 400 nm and to about 3 $\mu$m, at significant energy levels, in accordance with the blackbody radiation profile.

The present system uses one UV enhanced flashlamp, and greatly outperforms systems currently available. One UV enhanced flashlamp of the present invention is equivalent to about 250 of the current lamps. However, the current lamps only radiate at a few distinct wavelengths in the UV, while the lamps of the present invention radiates at all the UV wavelengths, as well as the visible and infrared, thereby providing a match for all of the significant atomic absorption bands of the contaminants. The UV efficiency of a typical lamp of the present invention is about 48% to about 52%. This is how much of the electrical energy applied to the flashlamp is converted into light energy. The visible efficiency is between about 25% and about 30% while the infrared is generally about 5% to about 10%. On contrast, current UV technology is about 5 to about 15% UV efficient at the three predominate wavelengths and these only radiate at rates in the millijoule/cm$^2$.

Because the present system operates with only one lamp, not hundreds, it is very compact. It can easily be placed in an area such as a gas station, business park, apartment complex, private home, or even a national park and not be an eye-sore or source of undesirable noise.

An application to which the present invention is particularly well suited is the photodegradation of methyl t-butyl ether (MTBE), an ether compound. Its primary use is as a gasoline additive. Its primary function is to increase the available oxygen during combustion while maintaining the octane rating of the fuel. The terminal end of this molecule is electronegative making it very soluble in water and therefore difficult to remove by conventional ion filtering or air-stripping.

Embodiments of the present invention range in size and capacity between small under-sink home units and large 700 gallon per minute systems for installation on municipal wells. Flashlamp replacement is at time intervals from between monthly on the large scale systems and yearly on the home products.

In a preferred embodiment, a 20 gallon per minute product addresses a high priority market: MTBE plume remediation. This embodiment can be used in conjunction with a shallow well that pumps groundwater from, for example a contaminated aquifer beneath leaking gas station storage tanks, treats it to remove the MTBE and then discharges the water back into the aquifer. The embodiment is small, self contained, weighs about 350 pounds, or more or less, and utilizes safety and self diagnostic features to ensure effective water treatment. A similar embodiment is used to target the small scale drinking and waste water treatment markets.

In another embodiment, a 700 gallon per minute embodiment services large scale domestic and foreign markets. When connected directly to the well head of a municipal water supply, this energy efficient embodiment will run continuously under the most adverse and varying conditions.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Near-Blackbody Radiator Means

Figure 1:
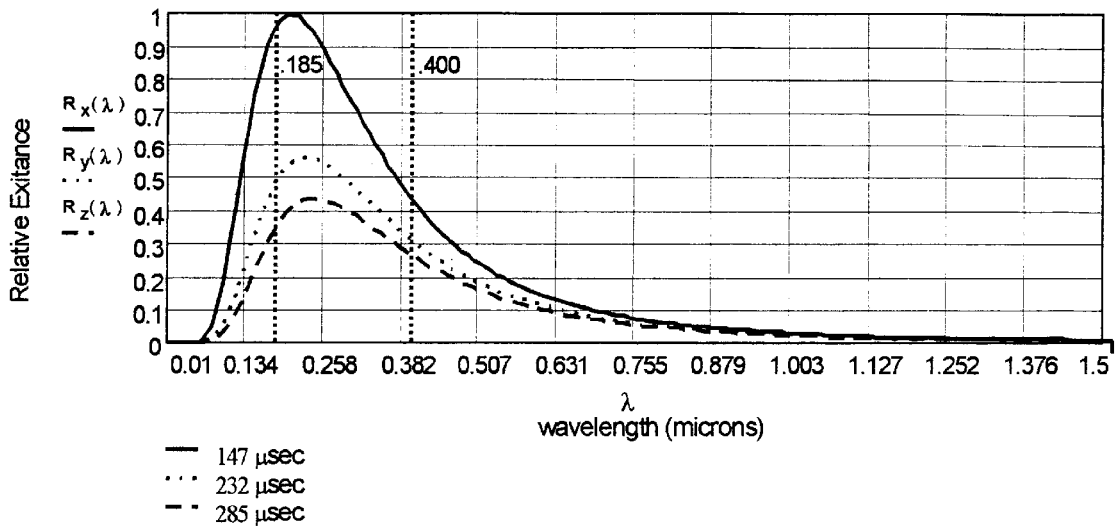
FIG. 1 is the blackbody response relative spectral exitance.

In a preferred embodiment of the present invention, a near-blackbody radiator means comprises a high peak power, high average power Xenon-gas filled flashlamp. Such a radiator means is capable of delivering up to 12 MW of peak power with average power up to 50 KW. The use of this type of flashlamp for photolytic decontamination of water is heretofore unknown. The power density of the Xenon-gas plasma inside the lamp produces a strong continuum output. Depending on the selected pulse duration and input energy, this continuum output has a peak in the near to far UV region. The Xenon-gas plasma temperature, again depending on the selected pulse duration and other factors, can range as high as 15,000° K. or higher. The diameter of the plasma is kept relatively small so that conversion efficiencies, particularly in the shorter wavelengths, are maximized.

The term "blackbody" denotes an ideal body which would, if it existed, absorb all and reflect none of the radiation falling upon it; its reflectivity would be zero and its absorptivity would be 100%. Such a body would, when illuminated, appear perfectly black and would be invisible, except its outline might be revealed by the obscuring of objects beyond. The chief interest attached to such a body lies in the character of the radiation emitted by it when heated, and the laws which govern the relations of the flux density and the spectral energy distribution of that radiation with varying temperature.

The total emission of radiant energy from a blackbody radiator takes place at a rate expressed by the Stefan-Boltzmann (fourth power) law; while its spectral energy distribution is described by Planck's equation and other empirical laws and formulas. Planck's law, often referred to as the fundamental law of quantum theory, expresses the essential concept that energy transfers associated with radiation such as light or x-rays are made up of discrete quanta or increments of energy proportional to the frequency of the corresponding radiation. This proportionality is usually expressed by the quantum formula $$E = h\nu \quad (1)$$

in which E is the value of the quantum in units of energy and ν is the frequency of the radiation. The constant of proportionality, h, is the elementary quantum of action, or Planck's constant.

The relationship:

$$E_\lambda d\lambda = \frac{hc^3}{\lambda^5} \frac{d\lambda}{e^{\frac{hc}{k\lambda T}} - 1} \quad (2)$$

is known as Planck's radiation formula, where $E_\lambda d\lambda$ is the intensity of radiation in the wavelength band between λ and (λ+dλ), h is Planck's constant, c is the velocity of light, k is the Boltzmann constant and T is the absolute temperature. This formula describes the spectral distribution of the radiation from a complete radiator or blackbody. This equation can be written in other forms, such as in terms of wavenumber instead of wavelength. It may also be written in terms of wavenumber instead of wavelength intensity.

The emissivity of the volume emitter (flashlamp plasma) is difficult to estimate accurately because of its strong dependence on temperature, wavelength and depth. Nonetheless, since the plasma reaches thermodynamic equilibrium very quickly during the pulse, and the depth, for all practical purposes, remains nearly constant during the period of equilibrium, the emissivity ε can be described according to wavelength interval. Hence, the express "near-blackbody radiator".

The flashlamp is designed to withstand these pulse durations over a long life providing pulse to pulse reliability. In general, to achieve a higher plasma temperature, for a given power rating the application of shorter pulses of energy will be useful. Radiative heat transfers are proportional to differences in temperature to the fourth power $$q \ T^4 - T_\infty^4 \quad (3)$$

The electron temperature $T_e$ of the resulting gas plasma inside the lamp is a function of the input energy $E_0$, the inside surface area of the lamp A, and the pulse duration $t_x$ and is given by the formula $$T_e = \left(\frac{0.9 E_0}{\sigma A t_x}\right)^{\frac{1}{4}} \quad (4)$$

where σ is the Stefan-Boltzman constant equivalent to $5.67 \times 10^{-12}$ watt/cm²/K⁴.

Total blackbody irradiance, a function of the pulse duration and the electron plasma temperature, is given by the formula $$Rt_x(Tx_e) = \sigma Tx_e^4 \quad (5)$$

Furthermore, the total power density of the lamp, i.e., the total power emitted by the lamp, including radiation from the emitter as well as thermal energy, will be given by the formula $$Px_\rho = \frac{E_0}{t_x A} \quad (6)$$

In a typical application, taking into account the lamp envelope and flow-tube losses, a preferred embodiment of the flashlamp system of the present invention will generate a radiant flux of broadband continuum radiation of about 12 MW peak. The spectral breakdown is as follows:

Approximately 51.2% of this radiant flux (6.2 MW) will be UV (185–400 nm).
Radiant exitance: 59,678 watt/cm², Dose exitance: 13.8 joule/cm², Dose flux: 1440 joule.
Approximately 24.6% (3.0 MW) will be in the VIS (400–700 nm).
Radiant exitance: 28,908 watt/cm², Dose exitance: 6.7 joule/cm², Dose flux: 697 joule.
Approximately 11.4% (1.39 MW) will be IR (700 nm–3 $\mu$m).
Radiant exitance: 13,313 watt/cm², Dose exitance: 3.1 joule/cm², Dose flux: 322 joule.

These radiant values indicate that one lamp can greatly exceed the dose requirements (0.6 watt•sec/cm² at 185 nm) to dissociate the bonds of organic molecules. Over the range of 185–400 nm, resonance bands for most organic interatomic bonds, dose values can be eighty times as high. One lamp provides dosage ranging from 50 to 6900 times greater than what is required for bacteria, mold, protozoa, yeast, and viruses.

In the case of photolytic redox, total oxidizable carbon (TOC) levels are reduced by the UV light creating free hydroxyl ·OH radicals, OH⁻ ions and peroxy radicals hydroxyl such as $O_2^-$ and $HO_2$ from water or oxidant additives. By way of the free radical chain mechanism performing electron or hydrogen atom abstraction, organic molecules are either dissociated or unsaturated and then oxidized into $CO_2$, $H_2O$, and in some cases, into various intermediate species. These intermediate species are prevalent in halogenated compounds such as the chlorinated solvents, pesticides, and herbicides. These intermediate compounds may include low concentrations of simple acids such HCl and HOCl. Compounds that are more complex may be formed if the free radical chain mechanism is not sustained.

The flashlamp UV system of the present invention is a relatively inexpensive way of destroying these dangerous chemicals. The lamplife is rated at 18–50 million shots, or approximately 1000 to 2800 hours. Target flow rate for a single lamp system is 1–5 million gallons/day (MGD) depending on the contaminant level.

The process of flashlamp photodegradation referred to in this paper as including photolytic oxidation/reduction (redox), is a complex series of steps taken in a specific order. Listed below are primary concerns of photolytic redox of contaminants in water:

Dosage

The contaminant bearing water must receive the proper amount of ultra-violet light. The longer the contaminated water is exposed to the actinic radiation the greater the dosage, and hence, the longer the free radical chain mechanism can be sustained for complete redox reactions.

Coefficient of Absorption

Lambert's law describes the decrease in light intensity with distance penetrated into a medium. Increase levels of TDS and turbidity exacerbate this problem of light transmission. The multi-pass reaction chamber design overcomes this obstacle by repeatedly bringing the water into close proximity with the lamp. For high coefficients of absorption (CoA) levels, this insures that during at least one-third of the retention time in the reaction chamber, the water is receiving 70% to 98% of the maximum light intensity available.

Oxidant

Insuring that there is enough oxidant available in the water to oxidize the contaminants is important. This includes considering TDS as contaminants. TDS do absorb ultraviolet and are likewise oxidized. TDS includes dissolved metals such as iron, manganese, zinc, sodium, calcium magnesium, aluminum, and copper. Sulfates and sulfur compounds and nitrates as well as the heavy metals, lead and mercury can also be present.

Experimental Method

To attain the spectral data, a ⅛ M 1200 L/mm grating monochromator with 280 $\mu$m slits for 2 nm resolution was used. The output of the monochromator was coupled to an UV enhanced silicon diode circuit.

The UV light was generated by a specialized flashlamp. The lamp arc-length was 335 mm with a bore of about 10 mm. The predominant fill gas was Xenon with a total gas fill pressure less than 1 Atm absolute. The cathode work function was 1.1 eV. The lamp was driven using a multi-sectioned PFN with pulse repetition rates ranging from 1 pps to 5 pps at full rated energy.

In order to measure and easily adjust parameters such as dosages, (CoA), and temperature, the reaction chamber was a scaled bench-top model. Testing of the water samples was performed by independent environmental laboratories using EPA approved 8010 and 8020 water testing methods.

Flashlamp Blackbody Radiation

A continuum mode of radiation is created by strongly ionizing the gas within the flashlamp. This continuum radiation approaches a high-emissivity blackbody radiation profile with increasing flashlamp power density. Power density is defined as:

$$P_\rho = \left( \frac{E_0}{t \cdot A_s} \right) \tag{7}$$

where:

$E_o$=lamp discharge energy (joules):

t=pulse duration full duration, half maximum (FWHD) (seconds); and $A_s$=lamp bore surface area (cm²).

Attaining a high emissivity ultra-violet blackbody response requires that power densities exceed about 50,000 watt/cm² with t≦about 1 msec. In a preferred embodiment, densities in test power densities ranged from about 127,000 watt/cm² to about 246,000 watt/cm² with about 155,000 watt/cm² being optimal. As the power density increases, the emissivity approaches unity in the UV bands. In the VIS and IR bands, high emissivity is easily achieved. Equation (7) shows that as the pulse duration increases, the power density decreases. Thus, as $E_o$ and $A_s$ are held constant, (t) becomes the primary method of adjusting the UV response of the lamp, principally by affecting the plasma temperature.

Using the minimum bound of 50,000 watt/cm², the upper bound, when expressed as wavelength, must be greater than the UV-cutoff of the lamp's envelope material. This is calculated by minimizing the percentage of UV generated that falls below the minimum UV-cutoff wavelength of the envelope. This energy is simply wasted in the lamp walls as heat, thus reducing lamplife and conversion efficiency.

Within this narrow pulse interval, one can calculate the exitance response of the lamp from Wien's Displacement Law and Plank's Radiation Law as follows:

Plasma temperature is determined by finding the peak wavelength over the UV interval and then applying Wien's Displacement Law:

$$T = \frac{2898}{\lambda_{peak}} \quad (8)$$

where:

T in Kelvin $\lambda_{peak}$ in microns

Using Plank's Radiation Law to determine the exitance over selected bandwidth:

$$R(\lambda) = \int_{\lambda_1}^{\lambda_2} \left[ \frac{37418}{\lambda^5 \left[ e^{\left(\frac{14388}{\lambda T}\right)} - 1 \right]} \right] \quad (9)$$

where:

$\lambda$=total wavelength interval, [185 . . . 3.00] $\mu$m;

$\lambda_1$=shorter wavelength in question;

$\lambda_2$=longer wavelength in question;

T=plasma temperature as determined by equation (8).

The normalized exitance over a selected bandwidth is given by Equation 10:

$$H_{bw} = \left[ \frac{R(\lambda)}{\sigma T^4} \right] \quad (10)$$

where:

$\sigma$=Stefan-Boltzmann constant, 5.67×10$^{-12}$ J cm$^{-2}$ K$^{-4}$ sec$^{-1}$; and T=plasma temperature as determined by equation (8).

The exitance at any wavelength is described by the Stefan-Boltzmann Law corrected for bandwidth concentrations:

$$R(T) = \lfloor \bar{\varepsilon}\bar{s}\sigma T^4 \rfloor H_{bw} \quad (11)$$

where:

$\bar{\varepsilon}$=average emissivity (0.98);

$\bar{s}$=average radiation efficiency (0.85);

$\sigma$=Stefan-Boltzmann constant, 5.67×10$^{31}$ $^{12}$ J cm$^{-2}$ K$^{-4}$ sec$^{-1}$ T=plasma temperature as determined by equation (7).

Using the lamp at 147 $\mu$sec, 232 $\mu$sec, and 285 $\mu$sec pulse durations, the plasma temperatures as determined by Wien's Displacement Law are about 14057 K, 12536 K, and 11916 K respectively. The following table summarizes the data:

TABLE 1

|  |  | t | $\lambda_{peak}$ | T | $H_{bw}$ | Exitance | Dosage | Flux |
|---|---|---|---|---|---|---|---|---|
| $R_a(\lambda)$ | uv | 147 | 206 | 14057 | 52.0% | 95896 | 14.1 | 1466 |
|  | vis |  |  |  | 20.6% | 38268 | 5.6 | 582 |
|  | IR |  |  |  | 8.7% | 16122 | 2.4 | 250 |
| $R_b(\lambda)$ | uv | 232 | 231 | 12536 | 51.2% | 59678 | 13.8 | 1435 |
|  | vis |  |  |  | 24.6% | 28908 | 6.7 | 697 |
|  | IR |  |  |  | 11.4% | 13313 | 3.1 | 322 |
| $R_c(\lambda)$ | uv | 285 | 243 | 11916 | 50.1% | 47729 | 13.6 | 1414 |
|  | vis |  |  |  | 26.5% | 25345 | 7.2 | 749 |
|  | IR |  |  |  | 12.8% | 12193 | 3.5 | 364 |

It is apparent from the tabulated data that the UV exitance values vary from 95896 watt/cm$^2$ at 147 $\mu$sec to 47729 watt/cm$^2$ at 285 $\mu$sec (about one half the value at 147 $\mu$sec). However, the dosage and conversion efficiency varies by no more than 4% in the UV band. This is a key design point. The shorter pulse greatly reduces the explosion energy maximum of the lamp thereby reducing lamplife. There is no significant gain in UV dosage by driving the lamp harder, i.e., by using shorter pulse durations. However, there is a significant decrease in lamplife.

Figure 2:
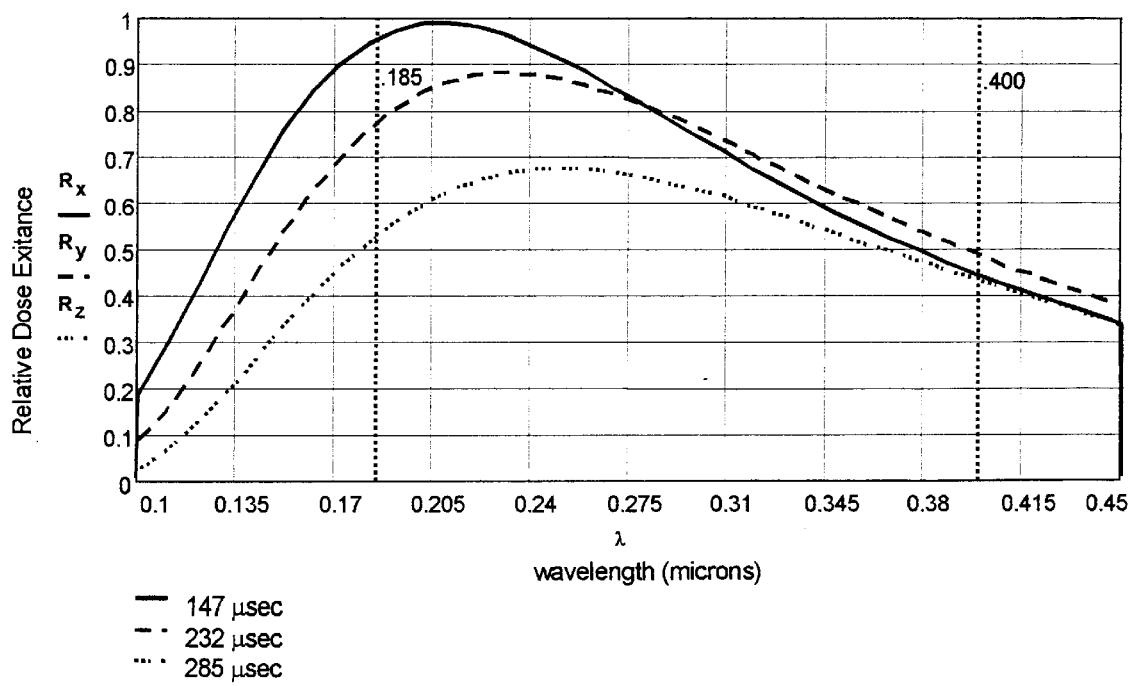
FIG. 2 illustrates the blackbody dosimetry response over the UV interval.

FIGS. 1 and 2 show the blackbody response at the three selected pulse durations. FIG. 1 is the relative spectral exitance and FIG. 2 illustrates the dosimetry response over the UV interval.

Flashlamp Lifetime

The flashlamp must be optimized to deliver the maximum amount of useful radiation with good conversion efficiency while still maintaining a useful long lamplife. Driving the lamp harder to produce even more UV shortens the lamplife considerably and may not be necessary. Careful attention must be paid to optimizing this trade-off of UV intensity and lamplife by adjusting pulse shape, duration, repetition rate, and energy input.

In order to maintain reasonable lamplife, the flashlamp's explosion energy must be kept below 18% of the theoretical single-shot explosion energy limit. The following formulas show how the explosion energy is related to the lamp geometry, envelope material, input energy and pulse duration.

The dimensions and envelope material of the flashlamp are used to develop a numerical coefficient that will aid in the calculation of the lamp-life. This number is the explosion-energy constant ($K_e$):

$$K_e = f(d)ld \quad (12)$$

where:

f(d)=quartz power function based on material transparency, thermal conductivity, wall thickness, and bore, W sec$^{1/2}$ cm$^{-2}$;

l=discharge length of the flashlamp, cm.; and d=bore of the flashlamp, cm.

The single-shot explosion energy:

$$E_x = K_e t^{1/2} \quad (13)$$

where:

t=pulse duration FDHM, seconds.

The lamp lifetime, in number of shots, is approximated by:

$$LT = \left[ \frac{E_o}{E_x} \right]^{-\beta} \quad (14)$$

where:

$E_o$=flashlamp input energy, Joules; and $\beta$=scalar based on the lamp bore and wall thickness.

Cost effectiveness dictates that the lamp operate for at least 1000 hours at 232 $\mu$sec or at 285 $\mu$sec. By exceeding these time periods, lamplife becomes unpredictable thereby increasing the probability of unexpected lamp failure. These failures are generally due to expended cathodes and, to a lesser degree, catastrophic envelope failure. Scheduling lamp changes at regular and planned intervals is more cost effective. While exceeding these ratings by 25% to 30% is permissible it is not generally recommended.

By substituting and solving algebraically the proceeding formulas, it is possible to arrive at the minimum and maximum pulse durations for optimal lamplife:

$LT_{min}$=1000 hours=3600·sec·hr$^{-1}$·1000·hr·5 shots·sec$^{-1}$= 18,000,000·shots $LT_{max}$=2800 hours=3600·sec·hr$^{-1}$·2800·hr·5 shots·sec$^{-1}$= 50,400,000·shots Minimum pulse duration for $LT_{min}$:

$$t_{min} = \frac{E_o^2}{\left[LT_{min}^{\left(\frac{-1}{\beta}\right)}\right]^2 \cdot K_e^2} \quad (15)$$

Maximum pulse duration for $LT_{max}$:

$$t_{max} = \frac{E_o^2}{\left[LT_{max}^{\left(\frac{-1}{\beta}\right)}\right]^2 \cdot K_e^2} \quad (16)$$

Thus:

$t_{min}$=232 μsec for 1000 hours operation; and $t_{max}$=285 μsec for 2800 hours operation.

Figure 3:
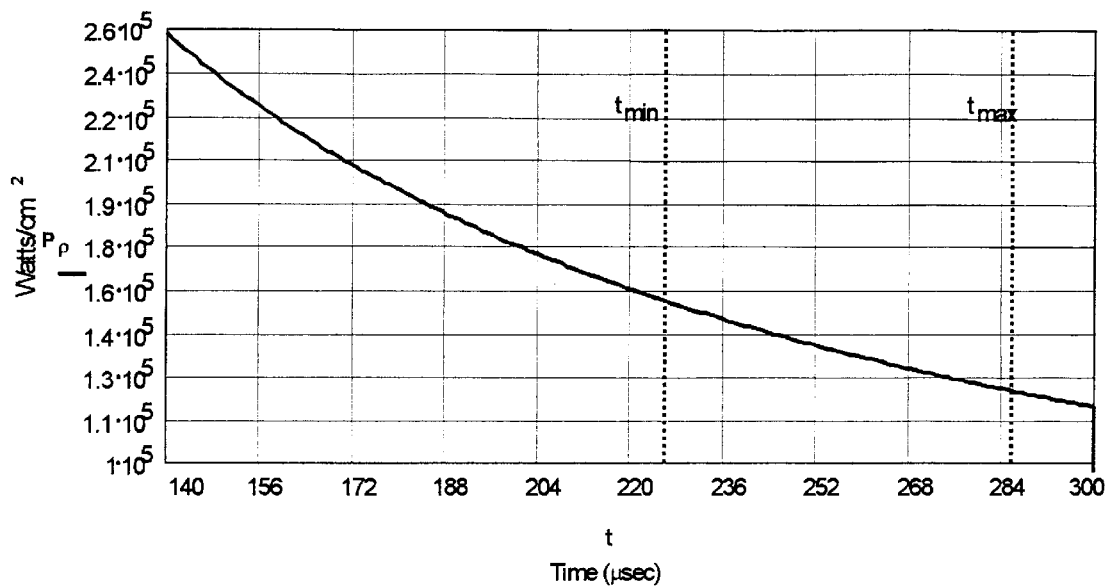
FIGS. 3 and 4 illustrate representative selected pulse durations against power density and lifetime curves.
Figure 4:
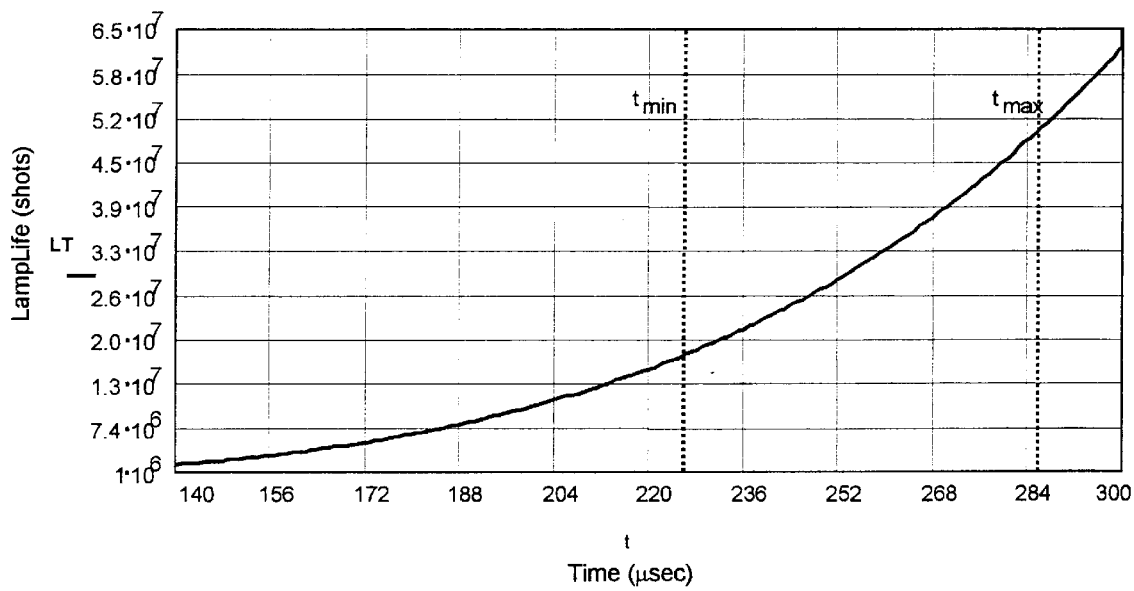

FIGS. 3 and 4 illustrate these pulse durations against power density and lifetime curves. By keeping the pulse duration confined to the interval [$t_{min}$, $t_{max}$], reliable lamplife is insured. The percentage of single-shot explosion energies for 147 μsec, 232 μsec, and 285 μsec are 18.6%, 14.8%, and 13.4%, respectively.

REACTION CHAMBER METHODOLOGY

Coefficient of Absorption

The TDS in water will determine how well the actinic radiation penetrates. The intensity (I) decreases with the distance (z) penetrated into the water according to Lambert's Law:

$$I = I_o \cdot e^{-\left(\frac{K \cdot 4 \cdot \pi}{\lambda}\right) z} \quad (17)$$

where:

$I_o$=incident radiation;

K=constant of proportionality;

λ=wavelength, (cm);

z=distance penetrated into medium (cm).

The quotient $$\left(\frac{K \cdot 4 \cdot \pi}{\lambda}\right)$$

comprises the coefficient of absorption (α).

Figure 5:
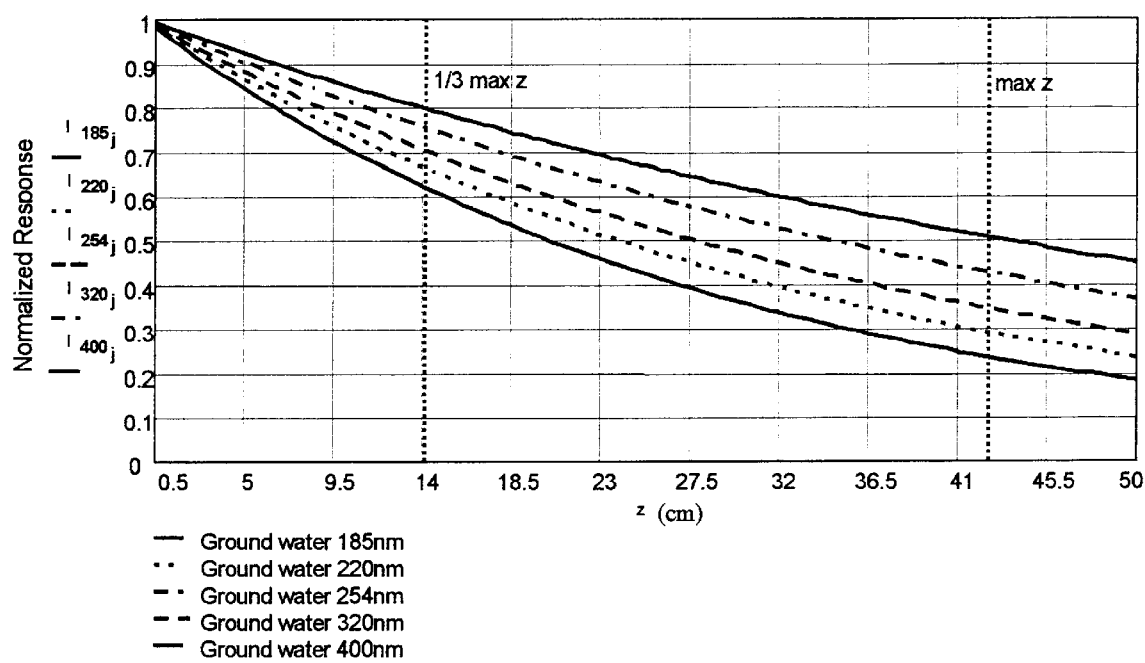
FIG. 5 illustrates general coefficient of absorption curves for ground water.

FIG. 5 shows that at a maximum distance (z) from the flashlamp, only about 40% of the energy reaches the contaminants. However, the water flows perpendicular and parallel to the lamp on several passes through the chamber, always insuring close contact with the lamp for at least ⅓ of the retention time. This multi-pass design allows heavy TDS water to receive high dosages of UV. In such high TDS water the energy delivered to flashlamp will be high as compared to low TDS water.

One way to improve system efficiency is to monitor the CoA through differential wavelength-selective measurements. By knowing the CoA and anticipated contaminant levels; adjustments can be made to the energy and/or pulse duration to reduce power cost and preserve the lamplife.

For measurement purposes the wavelength (λ) to measure is known but (K) is not. This is because we are unsure of the TDS. The CoA (α) can be expressed as:

$$\alpha = \frac{K \cdot 4 \cdot \pi}{\lambda} \quad (18)$$

then, by substitution into Equation (17):

$$I = I_o \cdot e^{\alpha z} \quad (19)$$

and solving for α:

$$\alpha = \frac{-\ln\left(\frac{I}{I_o}\right)}{\Delta z} \quad (20)$$

The value of ($I_o$) is normalized to the value of (I). Therefore, (I) is the closest sensor to the flashlamp. The sensors are filtered for 254 nm narrow bandpass and placed as far from each other as possible (Δz) but along the same axis. Once having solved for (α), (K) can now be determined:

$$K = \frac{\alpha \cdot \lambda}{4 \cdot \pi} \quad (21)$$

At this point, a CoA curve can be generated for any wavelength by using Equation (17). This information can then be fed to a control processor to adjust the flashlamp energy and/or pulse duration as needed, as well as water flow and oxidant infusion rates to enhance system efficiency.

Reaction Chamber Dosing

To provide the proper dosimetry to the contaminated water, the water must stay in contact with the light energy for some predetermined period of time. In addition, for cost effectiveness, the flow rate through the reaction chamber must be reasonably high. The minimum target flow rate for typical municipalities is about 1 MGD (690 gpm), or more or less. The pulse repetition rate is 5 pps. The volume of the reaction chamber must be large enough to retain the water for a sufficiently long enough period so that proper dosing takes place.

A scaled bench-top model parallels the phase-2 prototype reaction chamber. For prototype parameters of operation, the retention time is 7.7 seconds and the pulse factor is 38.5 pulses at 690 gpm.

Retention time is given by:

$$T_{ret} = \frac{V_{rc}}{flowrate} \quad (22)$$

where:

$V_{rc}$=reaction chamber volume (gal); and flowrate=gal/sec.

The number of pulses per $T_{ret}$ (pulse factor):

$$pf = prr \cdot T_{ret} \quad (23)$$

where:

prr=pulses per second.

Dose time:

$$t_i = pf \cdot t \quad (24)$$

where:

t=pulse duration FWHM (seconds).

The UV dose is found by:

$$D(\lambda) = \int_{\lambda_1}^{\lambda_2} \left[ \frac{37418}{\lambda^5 \left[ e^{\left(\frac{14388}{\lambda T}\right)} - 1 \right]} \right] \cdot \overline{\varepsilon} \cdot \overline{s} \cdot t_i \quad (25)$$

where:

λ=total wavelength interval, [0.185 . . . 3.00] μm;

$\lambda_1$=UV cutoff of envelope material (μm);

$\lambda_2$=0.400 μm;

T=plasma temperature as determined by equation (2);

ε=average emissivity (0.98);

s=average radiation efficiency (0.85);

$t_i$=dose time (seconds).

PHOTOLYTIC OXIDATION/REDUCTION

Redox Requirements

Photodegradation of contaminated water is not necessarily a straightforward process. The contamination may be due to any variety of hydrocarbon compounds including halocarbons, organic nitrogen, organic sulfur, and organic phosphorus compounds, or it may be microbial or inorganic in nature. The contamination may even be a combination of two or more of the groups just mentioned. This leads to formation of intermediate species during the photo-redox process, some of which are actually more hazardous than the original contaminant. In the case of halocarbons, vinyl chloride or ketones may be produced. In the case of MTBE, tertiary butyl alcohol (TBA), formic acid, acetic acid are produced.

One way to avoid the problem of large surpluses of unwanted intermediate oxidized species is to provide the following:

1. Dosage.
   a) Intense UV energy per pulse;
   b) High pulse repetition rate;
   c) High retention time and high flow rate (i.e., large volume reaction chamber); and
   d) Multi-pass configurations to insure those CoA extinctions are greatly minimized.
2. Oxidant.
   a) Optimal amount of oxidant is available with the UV dose to sustain the free radical chain mechanism. This process is necessary to oxidize the contaminants as completely as possible.
   b) The blackbody UV response provides radiation [185 nm, 400 nm] at megawatt levels. This in turn can generate:
      i Hydrated electron: $e^-_{aq}$;
      ii Singlet oxygen $^1O_2$ from ground state triplet $^3O_2$;
      iii Hydroxyl radical ·OH; and
      iv Peroxy radical $O^-_2$ or its conjugate acid $HO_2$.

The choice of oxidant will be dependent on the type and concentration of contaminant. Saturated oxygen, $O_3$ or $H_2O_2$ all have their uses. When these oxidants are use in conjunction with intense UV radiation, the above mentioned radicals are produced. When the oxidants are not irradiated, their effectiveness is greatly reduced, as there is no formation of the free radicals. A common but somewhat expensive method, at least for high contaminant concentrations, is the photolysis of $H_2O_2$ to be used as the oxidant. The following reaction illustrates this:

$$H_2O_2 + h\nu \rightarrow 2 \cdot OH \quad (26)$$

Two moles of hydroxyl free radicals ·OH are created from one mole of $H_2O_2$. The oxidation potential of ·OH is $E°=+3.06$, v making it even more reactive than $O_3$ in which, $E°=+2.0$ v. However, the cost effectiveness of using $H_2O_2$ has to be examined closely. If high concentrations are needed, then another oxidant should be considered. In general, the costs associated with such oxidants are relatively high.

Oxidation of MTBE

In the course of testing, focus was on MTBE (methyl t-butyl ether). MTBE is made by reacting methanol from natural gas with liquid phase isobutylene and heating with an acid catalyst at 100° C.:

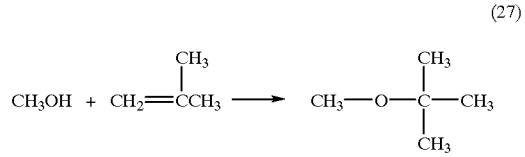

(27)

By applying the 285 μsec pulse as shown in Table 1, and scaling the dosage for one (1) MGD, the following results were achieved:

TABLE 3

| | Initial MTBE | $H_2O_2$ | Dose | Final MTBE |
|---|---|---|---|---|
| 1 | 45 | 40 | 225 | >5 (ND) |
| 2 | 1800 | 700 | 335 | >15 (ND) |
| 3 | 23000 | 26000 | 335 | (ND) |

ND = Not Detectable

In tests 1 and 2, no intermediate species were found during the 8020 test procedure. Minimal testing for intermediate species was performed. In test 3, no intermediate species were tested for. Intermediate species include low levels of formic and acetic acids.

System Layouts

Figure 6:
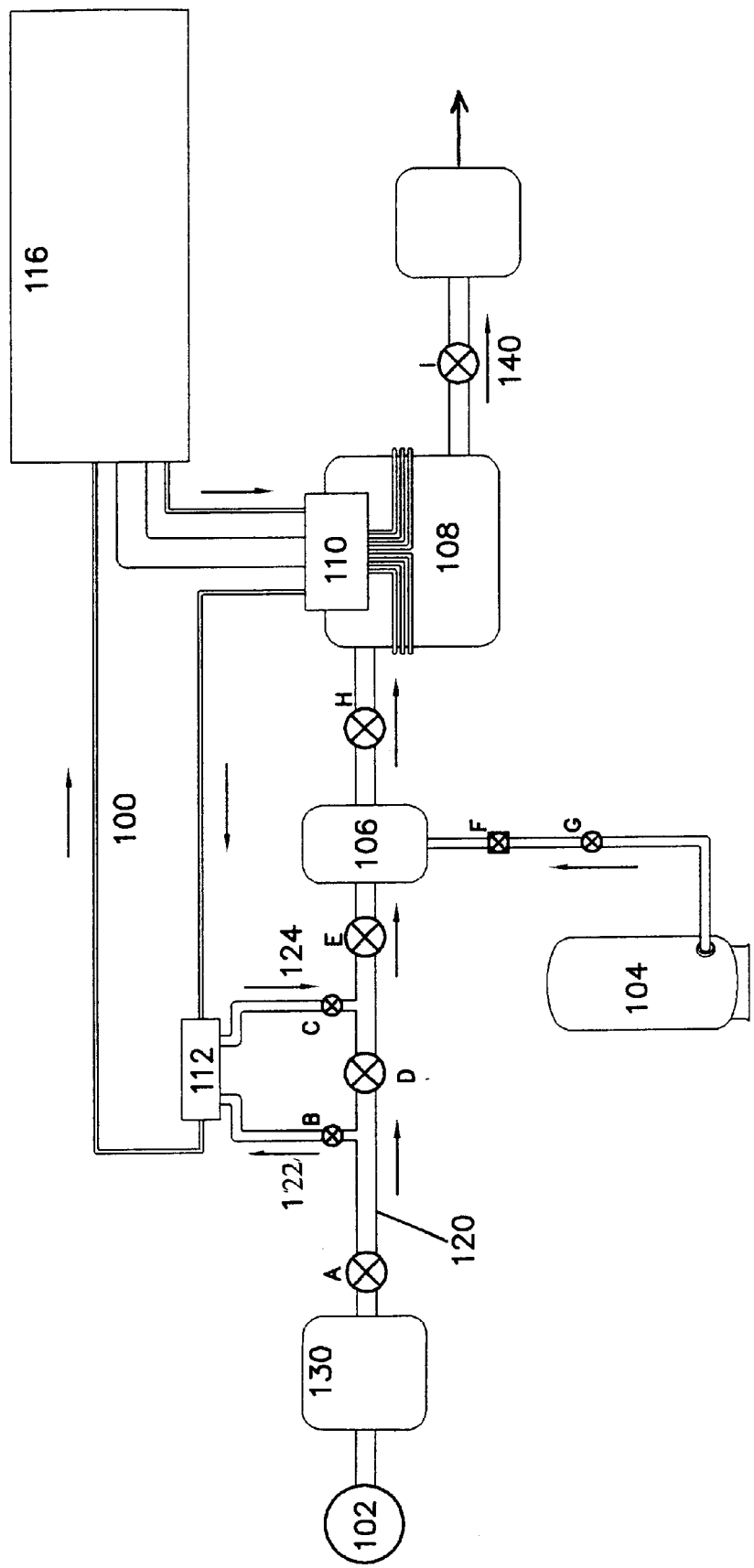
FIG. 6 is a representative field layout drawing of a preferred embodiment of the present invention showing photolytic redox method and apparatus for contaminated water remediation.
Figure 7:
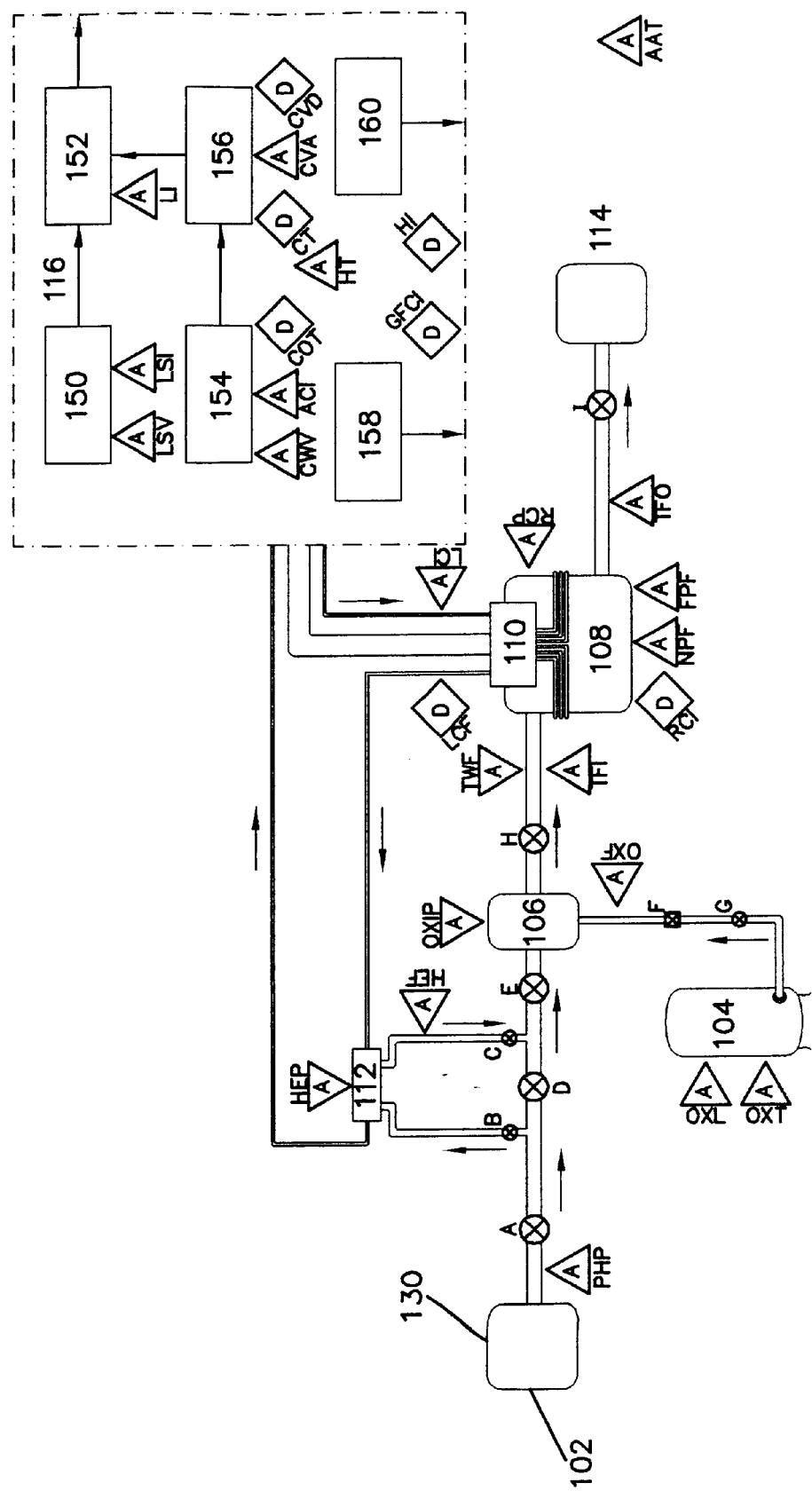
FIG. 7 is a representative sensor layout drawing of a preferred embodiment of the present invention for contaminated water remediation.

FIG. 6 is a representative field layout diagram showing photolytic oxidation method and apparatus for contaminated water remediation. FIG. 7 is a representative sensor layout drawing for contaminated water remediation. Water to be treated 102 enters with the system 100 via main flow control valve A. As described above, it is understood that such water to be treated 102 includes surface water from lakes, farming ponds and/or flooded areas, ground water including natural and artificial and/or otherwise created aquifers, storage tank water from private and public water supplies, water from water treatment facilities, such as a polishing loop in a chemical or processing plant effluence stream, and other specialized water source remediation and preparation, sources including semiconductor water supplies, and biomedical and pharmaceutical water supplies.

Proportioning valve D and isolation valves B and C and E control flow of water to be treated 102 through the system communicates. Oxidant storage vessel 104 stores chemical oxidant which can be introduced to the system 100. Such chemical oxidant material could be liquid hydrogen peroxide which is used as the oxidizing agent in the case of heavily contaminated water and/or for high flow rates thereof. Chemical oxidant from storage vessel 104 is metered through oxidant injector F into oxidant mixing vessel 106. The precise amount of chemical oxidant metered through injector F is controlled by the system controller. The required amount of chemical oxidant, such as hydrogen peroxide, is determined based upon, at least in part, one or more of, the following:

1. $H_2O_2$ concentration;
2. Contaminant concentration;
3. Flow rate of the treatable water:
    (a) Retention time in the reaction chamber;
    (b) Average dosimetry of each element of the flow;
4. Total dissolved solids (TDS) concentration;
5. Turbidity/optical density of the treatable water;
6. Temperature of the treatable water; and
7. Lamp output energy.

Within oxidant mixing vessel 106, chemical oxidant such as $H_2O_2$ is diffused evenly into the flow. Vessel 106 has sufficient volume to allow several seconds of turbulent mixing to help insure equilibration with the solute before entering reaction chamber 108. Lamp head 110 is mounted within reaction chamber 108.

Heat exchanger 112 uses at least part of the high flow rate of treatable water to remove excess heat from the closed-loop lamp cooling circuit of the system 100. A cooling fluid stream circulates through lamp head 110, according to system controller 116. Portions of the water to be treated 102 are directed through heat exchanger 112 to remove heat from the cooling fluid stream. By using this technique, no additional power or equipment is needed, thereby saving energy and equipment cost. The heat exchanger 112, optionally, is small and contains no moving parts.

Proportioning valve D divides the influent flow 120 past main flow control valve A so that some of the flow completes a circuit through heat exchanger 112, with flow of treatable water into heat exchanger 112 as shown by directional arrow 122 and flow out of heat exchanger 112 as shown by directional arrow 124. In a preferred embodiment, proportioning valve D does not increase the pressure head against the influent pump 130, or any gravity feed system, because the flow rate is not diminished but only divided between the two flow paths, flowing through either (a) valve D or (b) both valves B and C. Thus, heat is removed from the lamp head 110 cooling circuit and returned to the main flow. It will be understood that the treatable water is not contaminated by the cooling fluid passing through heat exchanger 112. Additionally, the slight additional heat added to the treatable water 102 enhances chemical decomposition and degradation of contaminants. Flow of purified water 140 is controlled by isolation valve I.

UV Dosage

Reaction chamber 108 contains the high-intensity UV-VIS near-blackbody radiator pulsed light source, hydraulic baffles, self cleaning mechanism, as well as optical and mechanical sensors and other measuring devices. It is demonstrated, therefore, how the volume selected for the reaction chamber 108 determines, at least in part and to a greater or lesser degree depending upon other considerations, effective retention time for the treatable water 102.

In preferred embodiments of the present invention, while baffle design is a factor which determines to a rather large degree dosage of energy from the light source within the reaction chamber 108, baffle design is less directly related to retention time in the chamber 108. With more particular regard thereto, total dosimetry is defined as:

$$D_{tot} = \frac{E \cdot T_{ret} \cdot prr}{A} \tag{28}$$

where:
(i) E=per pulse lamp radiation energy;
(ii) $T_{ret}$=retention time in reaction chamber;
(iii) prr =pulse repetition rate; and
(iv) A=surface area: lamp surface area, exposure area, etc.

Additionally, wavelength dependent dosimetry is defined as:

$$D(\lambda) = \int_{\lambda_1}^{\lambda_2} \left[ \frac{37418}{\lambda^5 \left[ e^{\left(\frac{14388}{\lambda T}\right)} - 1 \right]} \right] \cdot \bar{\varepsilon} \cdot \bar{s} \cdot t_i \tag{29}$$

where:
(i) $\lambda$=total wavelength interval, [0.185 ... 3.00] $\mu$m;
(ii) $\lambda_1$=shorter wavelength of interval;
(iii) $\lambda_2$=longer wavelength of interval;
(iv) T=plasma temperature as determined by Wien's displacement law;
(v) $\epsilon$=average emissivity of flashlamp plasma;
(vi) s=average radiation efficiency; and
(vii) $t_i=t \cdot T_{ret} \cdot prr$:
  1. t=pulse duration;
  2. $T_{ret}$=retention time in reaction chamber; and
  3. prr=pulse repetition rate.

System Control

A preferred embodiment of system controller 116 provides a signal from simmer supply circuit 150 to firing circuit 152. Output from charging supply circuit 154 is input to pulse forming network 156 which also is used in system control by firing circuit 152. System controller 116 additionally comprises lamp— *cooling pump control circuit 158 and controller 160.

A variety of electrical voltage and current sensors are provided in the system. In a preferred embodiment, ambient air temperature sensor AAT is an analog temperature sensor. Sensor AAT monitors for and determines freezing conditions which may effect the system, with a reference point established for purposes of control parameter calculations, etc., such as in normal operation. Housing temperature sensor HT, also an analog sensor in a preferred embodiment is provided, for purposes such as determination of excessive power dissipation, such as to ensure adequate heat to overcome ambient freezing conditions.

A safety circuit, in a preferred embodiment, would include a reaction chamber interlock RCI for preventing potentially hazardous or otherwise harmful radiation from being generated within reaction chamber 108 in the event a peripheral subsystem or component sensor failed to operate properly, and to interrupt operation or reaction therewithin in the event of failure of any peripheral subsystem or component. The reaction chamber interlock RCI is typically a digital sensor, and is associated with a digital signal indicator, such as part of the safety circuit. In a preferred embodiment, the system shuts down and dumps energy if the reaction chamber is opened or leaks. Such safety system would also include, in preferred embodiments, an overall ground fault circuit interrupter GFCI and associated or independent housing interlock HI circuits or controllers, as part of system controller 116 as shown. The overall ground fault circuit interrupter GFCI is typically a digital sensor, and is associated with a digital signal indicator, such as a redundant part of the safety circuit. In a preferred embodiment, the system shuts down and dumps energy if a ground fault is detected. The independent housing interlock HI is typically a digital sensor, and is associated with a digital signal indicator, such as a redundant part of the safety circuit. In a preferred embodiment, the system shuts down and dumps energy if power supply housing is opened or otherwise disturbed during operation.

System controller would also include capacitor voltage A sensor CVA and capacitor voltage D sensor CVD as input signal generators to pulse forming network circuit 156, lamp simmer voltage sensor LSV as input signal generator for simmer supply circuit 150, and charging waveform voltage sensor CWV as input signal generator to charging supply circuit 154. Capacitor voltage A sensor CVA, typically an analog signal device, is useful for monitoring energy use, such as to ensure operation with the specifications for driving the lamps of the present invention. Sensor CVD, such as a digital signal indicator, is also part of a safety circuit. Capacitor voltage D sensor CVD actuates a solenoid lock while the system is being charged and an energy dump circuit (EDC) is not actuated or is malfunctioning. Lamp simmer voltage sensor LSV determines whether the flashlamp is simmering or not, and if so, whether or not the simmer voltage is within normal operating specifications. Charging waveform voltage sensor CWV is used for determining quench timing, and to determine whether or not the voltage is within normal operating specifications. Current sensors include lamp current sensor LI, lamp simmer current sensor LSI and average charging current sensor ACI. Lamp current sensor LI determines whether the current supplied to the lamp is within normal operating specification, and is also useful for monitoring for reverse current conditions. Lamp simmer current sensor LSI determines whether the flashlamp is simmering or not, and if so, whether or not the simmer current is within normal operating specifications. Sensor LSI also determines the retrigger status of the system. Capacitor temperature sensor CT, typically a digital sensor, is associated with a digital signal indicator, such as part of the safety circuit. In a preferred embodiment, the system is associated with an interlock and is designed to shut down if the capacitors overheat.

Integrated Optical Feedback

The integrated optical feedback system implemented in a preferred embodiment of the present invention has capability for determination of the opacity and/or optical density of the treatable water at various wavelengths by using differential photo-feedback analysis (DPFA). This information is then used to determine the optimum flow rate and oxidant doping rate. In addition, the quality of light can be assessed to aid in system troubleshooting. Sensors mounted on or adjacent to reaction chamber 108 include a near photo feedback sensor NPF and a far photo feedback sensor FPF. The near photo feedback sensor NPF and the far photo feedback sensor FPF used for differential analysis of the treatable water's total dissolved solids (TDS) concentration.

The DPFA is a double photo type detector that has been narrow-pass and neutral density filtered for a specific wavelength (such as 254 nm) or band of wavelengths (such as 185 nm to 400 nm, etc.). One detector is placed adjacent or very close to the lamp, and the other is placed closer to or adjacent the outer edge of the reaction chamber. The distances between them as well as the wavelengths involved are known or can be determined.

Relative voltages and/or currents are generated from each of the detectors that are directly proportional to the light intensity at the specific wavelength; the closer detector generating more voltage and/or current than the farther one. For calculation purposes, the voltages and/or currents can be numerically normalized, such as to the voltage and/or current value of the closer detector. By using this differential method, recalibration due to the lamp aging is not necessary.

The differential voltage and/or current values represent the attenuation factor of the light as it travels to the outer walls of the reaction chamber 108. This is the coefficient of absorption (CoA). By applying Lambert's law, the amount of absorption at various distances can be calculated. This information is then used to adjust flow and energy. Thus, the detectors, especially the one closest to the lamp, can be used to determine the absolute output of the lamp after the CoA (or $\alpha$) of the flow is determined. This will aid in determining the optimum flow as well as monitoring the lamp performance.

Pressure and Flow

Water pressure and flow of fluid through the system and system components are measured and adjusted with transducers and solenoid valves. Optimum performance is achieved by adjusting the flow by way of the solenoid valves based on the feedback information from the DPFA as well as pressure transducers.

Pump head pressure sensor PHP is positioned to read the pressure of the water to be treated 102, and is useful for maintaining the pump head pressure within safety and operating limits. Heat exchanger flow rate sensor HEF measures the flow of fluid from heat exchanger 112 through isolation valve C and the pressure in the heat exchanger 112 is measured by heat exchanger pressure gauge sensor HEP. Heat exchanger pressure gauge sensor HEP is used, in a preferred embodiment, to ensure operation within safety boundaries. Heat exchanger flow rate sensor HEF is used to determine adequate flow of cooling water for heat removal from the lamp head 110 heat exchanger. Lamp cooling water flow rate is measured by lamp cooling flow sensor LCF and lamp cooling water temperature is measured, in a preferred embodiment, adjacent at least one point, such as by lamp cooling flow inlet temperature sensor LCI. Lamp cooling flow meter sensor LCF, typically a digital sensor, is associated with a digital signal indicator, such as part of the safety circuit. In a preferred embodiment, the system is associated with an interlock and is designed to shut down power to the lamp if flow is inadequate. Sensor LCI is useful for ensuring an adequate cooling of the lamp.

Oxidant level sensor OXL measures the level or other value related to the remaining liquid oxidant in oxidant storage vessel 104, and oxidant flow meter OXF determines flow rate of oxidant from storage vessel 104 to oxidant mixing vessel 106. Sensor OXL also determines if oxidant storage vessel 104 needs recharging. The signal from meter OXF is useful in reaction balance determinations, and for measuring and controlling the oxidant volume consumed by the system. Oxidant infusion pressure sensor OXIP measures the pressure of the oxidant at or near the point of infusion of oxidant into oxidant mixing vessel 106, as indicated. OXIP is, in a preferred embodiment, an analog pressure gauge, useful in determination of reaction rates, and to ensure operation within safety and other parameters.

Treatable water flow meter TWF measure flow rate of treatable water downstream of isolation valve H prior to entry into reaction chamber 108. Sensor TWF is preferably analog, is useful for determination of reaction rates, pump head boundaries and treatment rates. The temperature of the treatable water feeding reaction chamber 108 is measured by treatable flow inlet temperature sensor TFI, typically an analog sensor. TFI is an important factor in the determination of reaction rates, with a reference point typically established in the system. The temperature of the treated water leaving reaction chamber 108 is measured by treatable water flow outlet temperature sensor TFO, also typically an analog sensor. A reference point is also typically established relative to the TFO. Reaction chamber 108 operating pressure is measured by reaction chamber pressure sensor RCP. An analog sensor for the reaction chamber pressure sensor RCP is typically used, such as for determination of reaction rates, safety limits of operation, and treatment rates. The temperature of the treated water is measured downstream of reaction chamber 108, preferably between reaction chamber 108 and isolation valve I.

Reaction Chamber and Lamp Assembly Design

Figure 8:
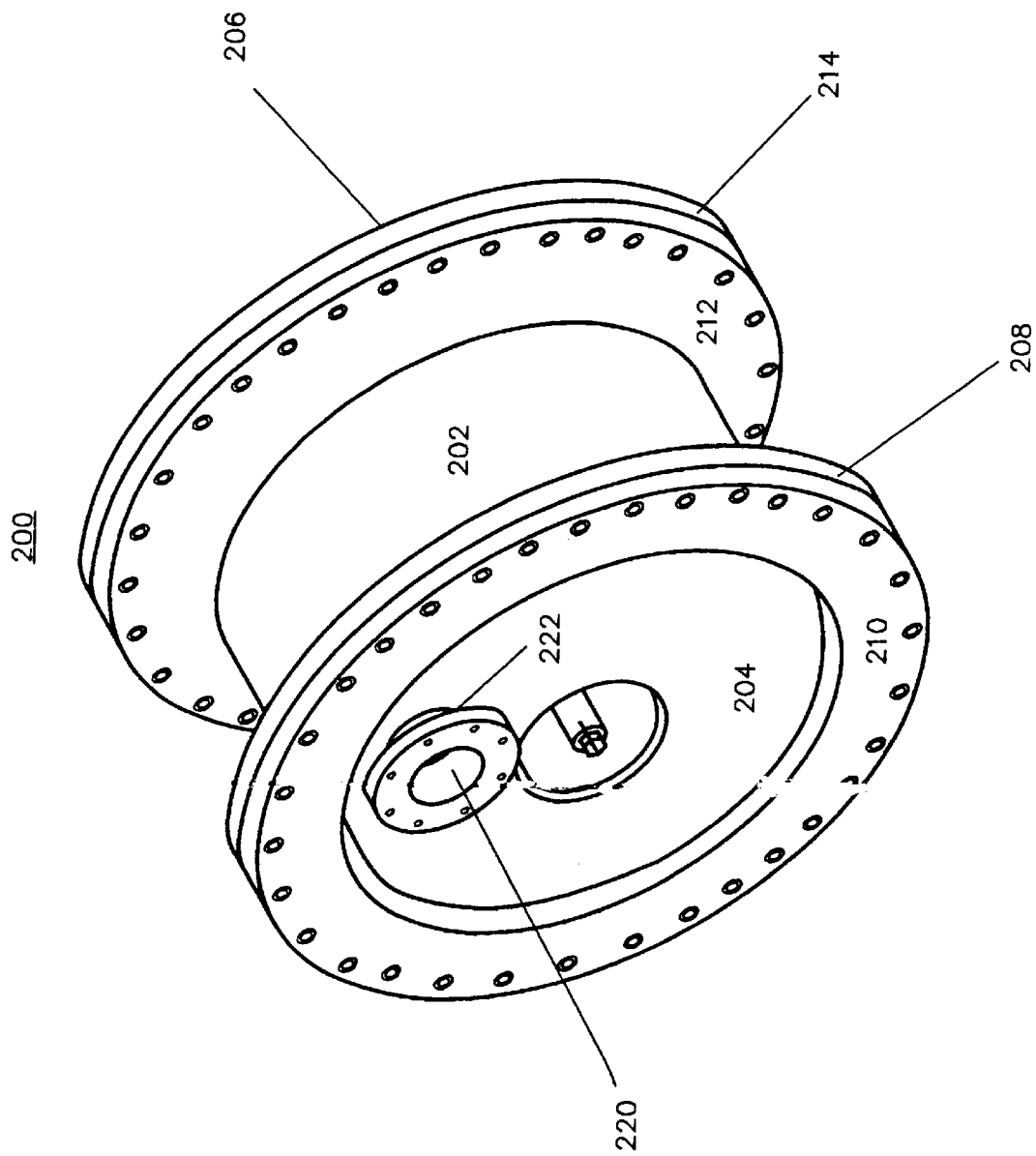
FIG. 8 is a representative isometric view of a preferred embodiment of a reaction chamber of the present invention.
Figure 9:
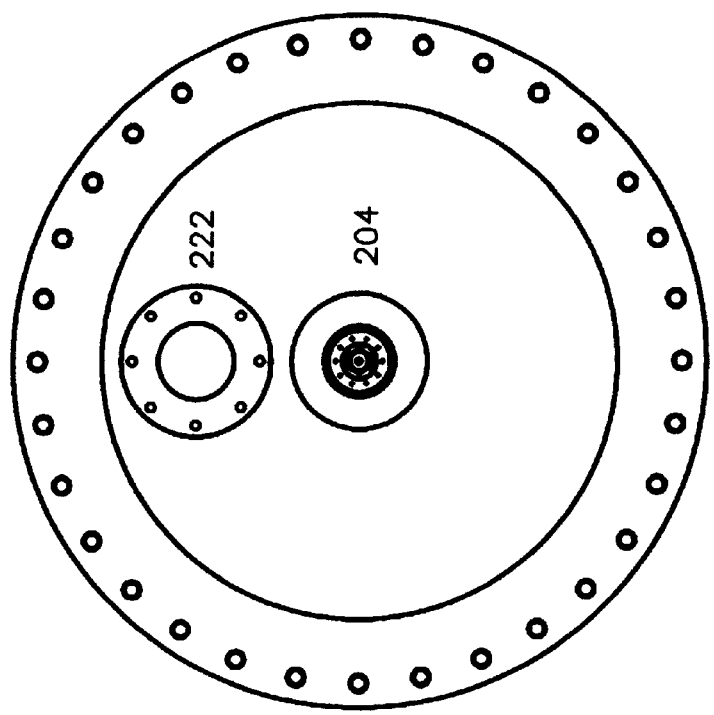
FIG. 9 is a representative front end view of a preferred embodiment of a reaction chamber such as shown in FIG. 8.
Figure 10:
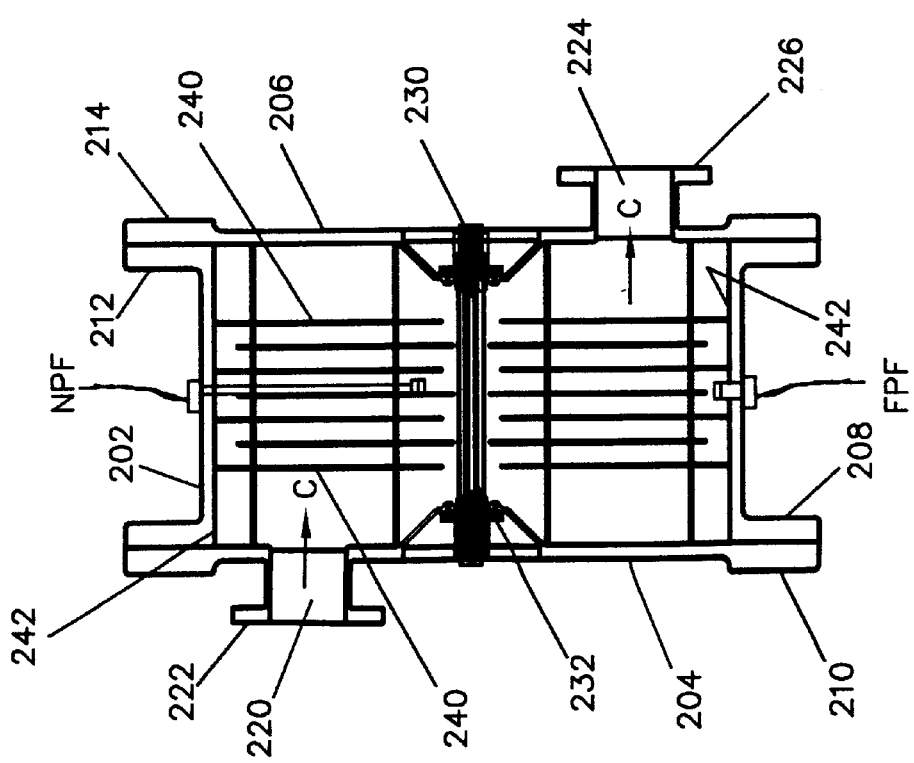
FIG. 10 is a representative section view of a preferred embodiment of a reaction chamber such as shown in FIG. 8.

FIG. 8 is a representative isometric view of a preferred embodiment of a reaction chamber of the present invention. FIG. 9 is a representative front end view of a preferred embodiment of a reaction chamber such as shown in FIG. 8. FIG. 10 is a representative section view of a preferred embodiment of a reaction chamber such a shown in FIG. 8.

Reaction chamber 200 is formed of an essentially cylindrical housing 202 with inlet side end plate 204 and outlet side end plate 206. Peripheral flanged portions 208 and 210 of cylindrical housing 202 and inlet side end plate 204, respectively, are coupled together in the familiar bolted, gasket optional, configuration as shown, as are peripheral flanged portions 212 and 214 of cylindrical housing 202 and outlet side end plate 206, respectively. Treatable fluid flow inlet 220 has a flanged face 222 and is mounted onto the inlet side end plate 204. Treated fluid flow outlet 224 also has a flanged face 226 and is mounted onto the outlet side end plate 206. Near photo-feedback sensor NPF and far photo-feedback sensor FPF are mounted as shown. A lamp assembly 230 is mounted to and between the inlet side end plate 204 and outlet side end plate 206, such that flashlamp tube 232 is disposed essentially centrally and aligned axially with the cylindrical housing 202. An internal baffle assembly is comprised of a plurality of operatively spaced baffle elements 240. Such baffle elements have any operative size and geometry, although it will be understood that, as shown, a preferred embodiment of the baffle elements 240 is essentially round and mounted within cylindrical housing 202. In a multi-pass design, the plurality of individual baffle elements 240 are mounted alternatingly spaced adjacent the inner wall 242 of cylindrical housing 202 and adjacent the flashlamp tube 232. Thus, flow of fluid, such as water, being treated withing reaction chamber 200 flows into reaction chamber 200 through inlet 220, following a route defined by directional arrows C and through outlet 224.

Figure 11:
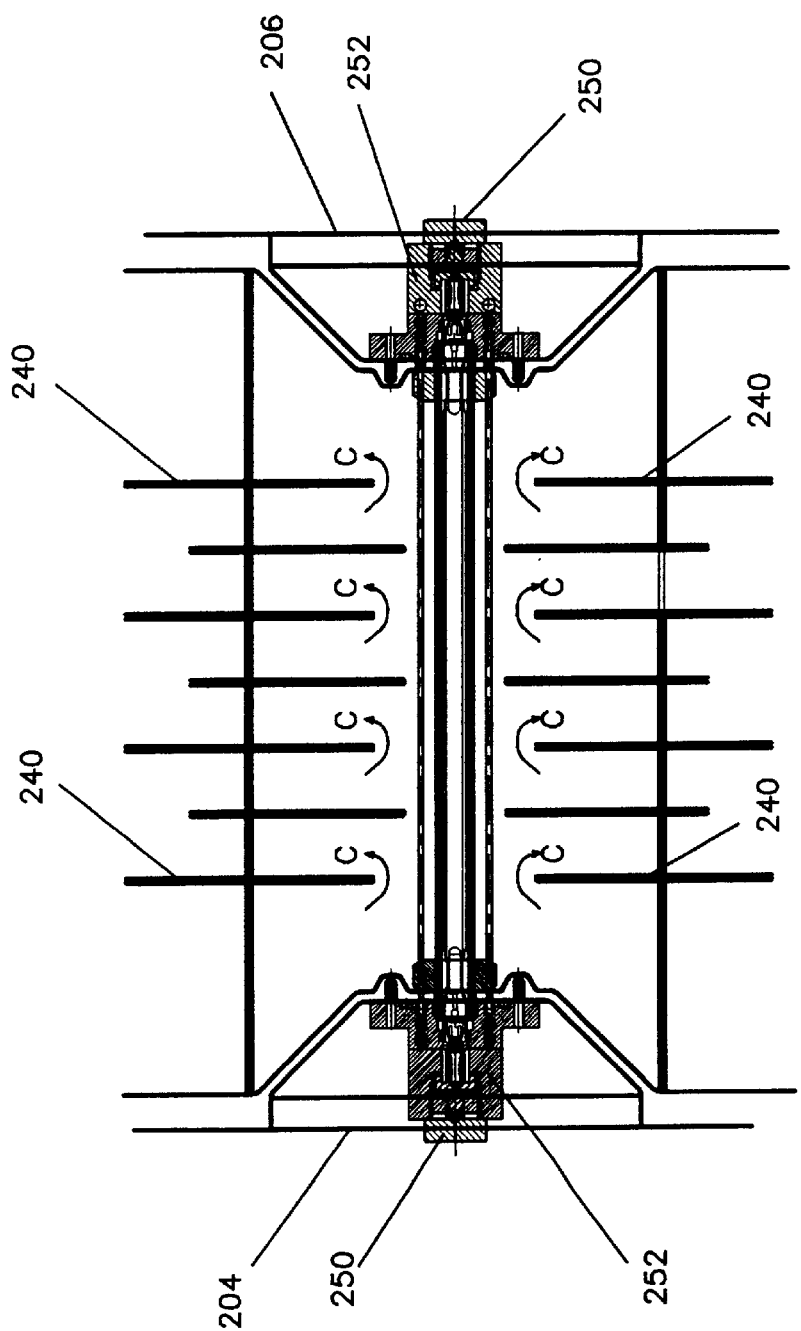
FIG. 11 is a representative section view of a preferred embodiment of a lamp head of a reaction chamber such as shown in FIG. 8.
Figure 12:
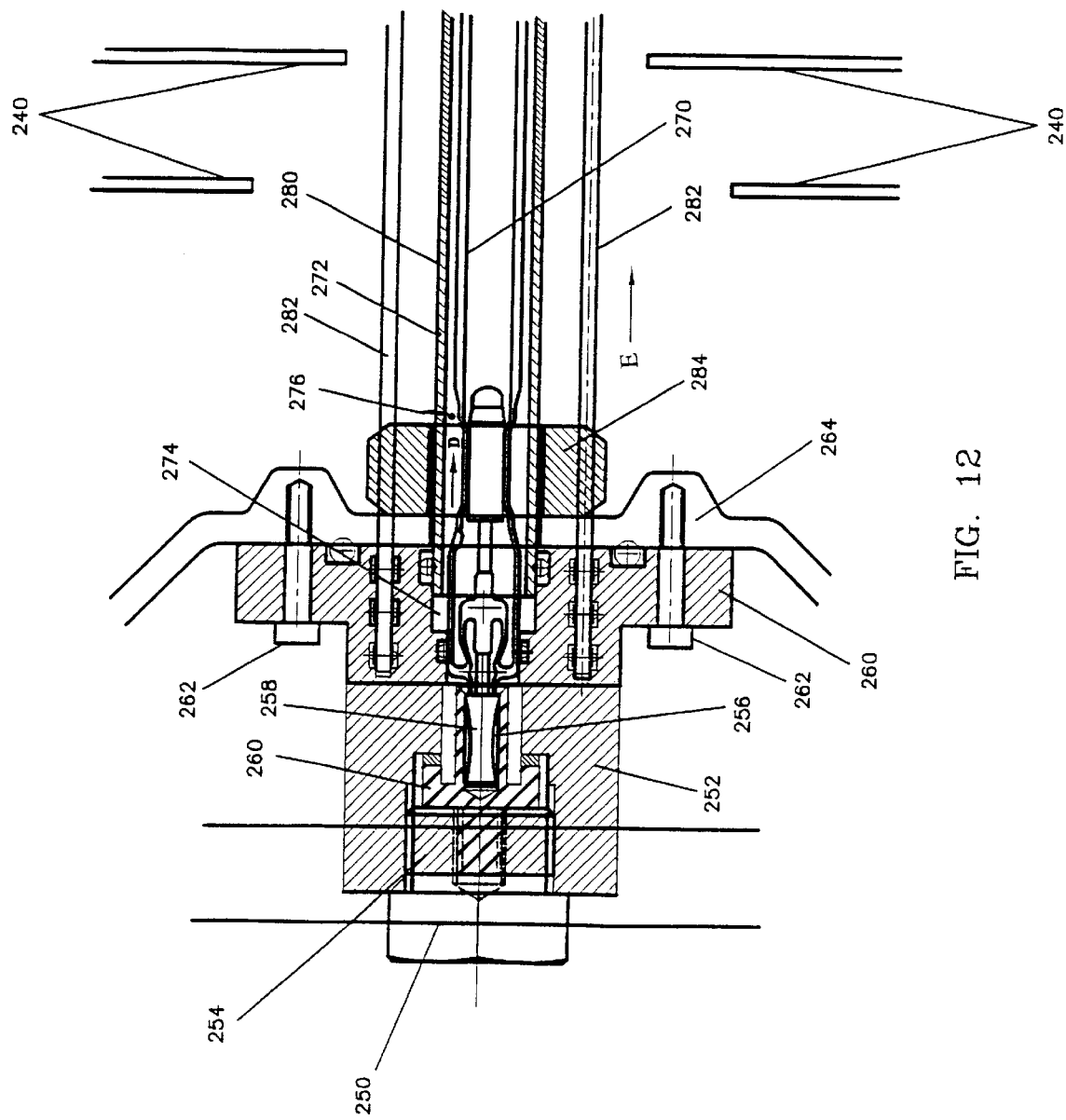
FIG. 12 is a representative detail view of a lamp head, such as shown in FIG. 11.

FIG. 11 is a representative section view of a preferred embodiment of a lamp head of a reaction chamber such as shown in FIG. 8. FIG. 12 is a representative detail view of a lamp head such as shown in of FIG. 11. As will be understood, the lamp assembly 230 shown in FIGS. 8–10 comprises a Teflon or other essentially non-conductive material end caps 250 mounted within either inlet side end plate 204 or outlet side end plate 206. Electrical power supply 252 is connected to the lamp via conductive connector element 254. Leaf-type spring members 256, optionally made of a beryllium-copper or other suitable alloy, form an excellent electrical and mechanical contact with the machined end, anode or cathode ferrules 258. Compressible ring lug 260 forms a seal between the end of conductive connector element 254 and power supply 252. Ceramic or other sturdy, non-conducting material end caps 260 support the assembly with bolts 262 or other retaining means which mount the assembly onto central flange portion 264 of either inlet side end plate 204 or outlet side end plate 206. Such central flanged portions 254 of the inlet side end and outlet side end plates 204 and 206 are made of a sturdy material such as steel.

As shown, the lamp tube 270 of the assembly 230 is disposed within flow tube 272. Cooling water is circulated through flow tube 272, entering the assembly through input ports 274 and passing through the annular region 276 between lamp tube 270 and flow tube 272, in direction D as shown. It will be understood that for illustrative purposes only one end of the lamp assembly 230 is shown in FIG. 12 and that flow of cooling fluid between lamp tube 270 and flow tube 272 will in most cases be from one end, such as the cathode end or the anode end, to the other end of the lamp assembly 230.

Since adhesions of contaminants in various states of decomposition may tend to foul the outer surface 280 of flow tube 272, a flow tube wiping system has been implemented in the preferred embodiment of the present invention. Rotating drive shafts 282 mount within end caps 260. By providing axial positioning means, such as a helically threaded groove on the outer surface of the drive shafts 282, a brush member 284 with corresponding helically threaded ridge therein can be made to move in direction E by rotating drive shafts 282 in a first direction. Reversal of said first direction will therefore cause motion of the brush member 284 in the opposite direction. It will be understood, however, that the described means for lateral wiping motion of the brush member 284 can be replaced or augmented by other suitable mechanical, electrical or hydraulic means.

Photo Feedback Based Control Flowchart

Figure 13:
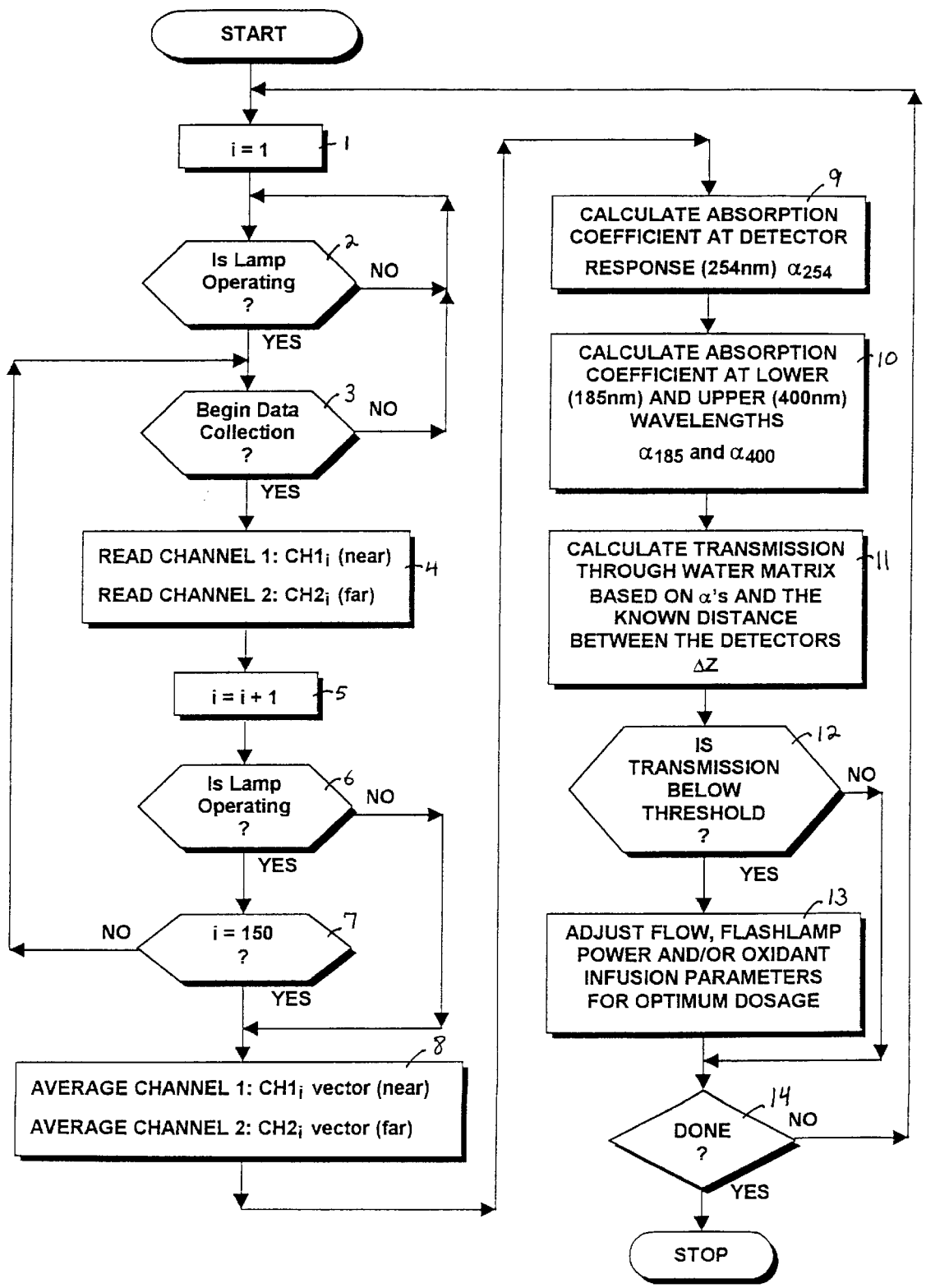
FIG. 13 is a flow chart that shows how flow rate, lamp power and oxidant infusion, among other operating parameters, are adjusted from predetermined values to calculated values based on differential photo feedback signals obtained during operation.
Figure 14:
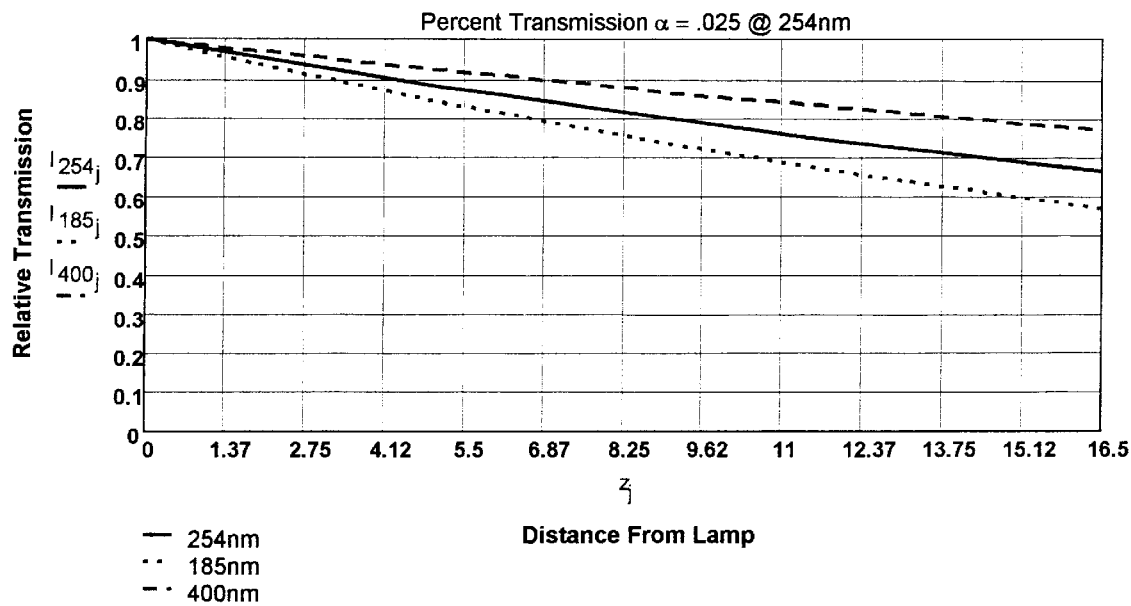
FIG. 14 illustrates a response curve of a preferred embodiment of the present invention for relatively light TDS concentration.
Figure 15:
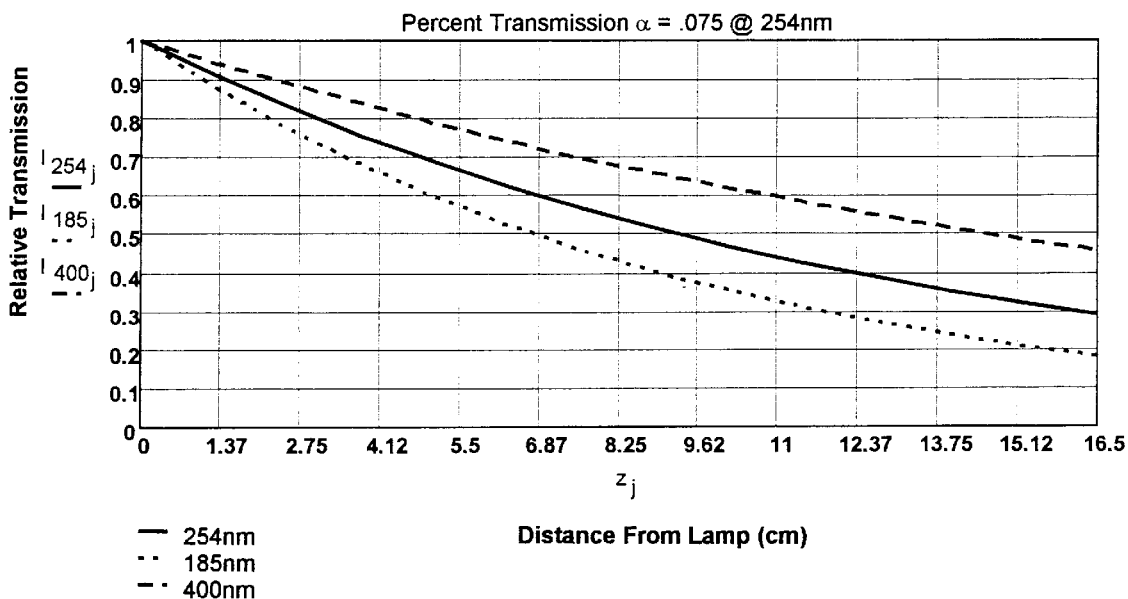
FIG. 15 illustrates a response curve of a preferred embodiment of the present invention for a heavy TDS concentration.

FIG. 13 is a flow chart that shows how flow rate, lamp power and oxidant infusion, among other operating parameters, are adjusted from predetermined values to calculated values based on differential photo feedback signals obtained during operation. It will be understood based upon the foregoing and following that the operating parameters selected and described with regard to the preferred embodiment of the present invention are only representative of a very large number of possible different parameters, and that, therefore, other combinations will be possible and known to those skilled in the art.

In a first step, a counter is initialized. Lamp operation, including normal pulsing, is confirmed in a second step. It will be understood that while in certain embodiments of the present invention there may be a single, normal operation mode, others will include plural, cascaded, parallel, serial or sequential, or other or multiple normal lamp operations, including but not limited in any way to various modes of operation such as normal operation, low-, medium- or high-pulse rate operation, programmed sequence operation, remote operation and/or control, stand-by operation, test operation, start-up operation, maintenance cycle, etc.

Thirdly, data is collected. A sequence is began to measure voltages from detectors as amplified by transimpedence amplifiers, etc. This includes the fourth step of incrementing the index, and the fifth step of measuring and storing the light energy values. In the case of a measuring cycle set to 30 seconds and a pulse rate of 5 pulses per second, a 150-pulse sequence is begun. Voltage or other determined value is read from a first channel, CH1 for each of values $CH1_1$ to $CH1_i$, with the determined value stored in the $i^{th}$ index of vector CH1. This will correspond with the first pulse of the 150-pulse measuring cycle or sequence. Simultaneously, voltage or other determined value is read from a second channel, CH2 for each of values $CH2_1$ to CH2$_i$, with the determined value stored in the i$^{th}$ index of vector CH2. This also corresponds with the first pulse of the 150-pulse measuring cycle or sequence. Therefore, when CH1 is a closer detector to the lamp (about 0.5" for example), and CH2 is a more distally positioned detector (such as about 5–15" or more or less), the distance ΔZ is the distance between the detectors and is known and is constant.

In a sixth step, lamp operation is confirmed, and, as in step 2, normal operation may be a function of a pre-programmed or programmable operation or other mode. In the event the lamp is not operating, for whatever reason, data collected to that point in operation will be collected and evaluated. Proceed to step 8. Otherwise, if lamp operation and/or function is normal, proceed to step 7.

Step 7 determines whether the counter has reached the end of its cycle, namely does i=150. If the 150th index of channel 1 and 2 vectors has been filled, proceed to step 8. Otherwise, check to see if a user-caused or system-caused interruption in data collection has occurred (step 3), and if not, proceed through sequence step 4, step 5, step 6 and step 7 until finished filling vectors for CH1 and CH2. In step 8, vectors are averaged over the number of valid indexes.

Step 9 is a calculation of the absorption coefficient. For example, $\alpha_{254}$ is the absorption coefficient at 254 nm, and the detector response is optimized for 254±20 nm. Based upon Lambert's law of equation (17):

$$\alpha_{254} = \frac{-\mathrm{Ln}\left(\frac{CH2\ \mathrm{Avg}}{CH1\ \mathrm{Avg}}\right)}{\Delta Z} \Rightarrow \text{(Lambert's Law)} \tag{30}$$

$$\alpha = \frac{-\mathrm{Ln}\left(\frac{I}{I_o}\right)}{\Delta Z}$$

In step 10, the absorption coefficient at lower wavelengths (such as at about 185 nm) and at upper wavelengths (such as at about 400 nm) is calculated. Since the 2 detectors are optimized for about 254 nm, neither opacity at about 185 nm nor at about 400 nm can be measured directly. More detectors could be added, but that would be a costly solution, with greater chance for error with more detectors and more software compute cycles to be performed. A better solution is to calculate the other opacities based on Maxwell's equations.

The absorption coefficients $\alpha_{185}$ and $\alpha_{400}$ can be found by comparing Lambert's law results for the decrease in light intensity with distance ΔZ penetrated into a medium:

$$I = I_o e^{-\alpha \cdot \Delta Z} \tag{31}$$

with the equations for the intensity obtained from the solution of Maxwell's equations. Since Maxwell's equations predict that for a wave traveling through a medium or matrix in the ΔZ direction:

$$A = A_o e^{j(\omega t - \hat{k} z)} \tag{32}$$

where:

$$\hat{k} = \frac{\omega}{c}\hat{n} = \frac{\omega}{c}(n - jk) \tag{33}$$

By substitution of equation (33) into equation (32):

$$A = A_o e^{j\left(\omega t - \frac{\omega n}{c} z + \frac{\omega}{c} jkz\right)} \tag{34}$$

and simplifying:

$$A = A_o e^{-\frac{\omega k}{c} z} \cdot e^{j\omega\left(t - \frac{n}{c} z\right)} \tag{35}$$

Therefore, the wave amplitude decreases exponentially with distance ΔZ. The intensity of radiated light is proportional to the square of the field (wave) amplitude. Thus, ignoring the complex term in equation (34):

$$A = A_o \left[ e^{-\frac{\omega k}{c} z} \right]^2 \tag{36}$$

$$= A_o e^{-2\frac{\omega k}{c} z} \tag{37}$$

By substituting into Lambert's law:

$$I = I_o e^{-2\frac{\omega k}{c} z} \tag{38}$$

and comparing equations (31) and (38):

$$\alpha = \frac{2\omega k}{c} \tag{39}$$

in which ω is the angular frequency:

$$\omega = \frac{2\pi c}{\lambda} \tag{40}$$

Thus, by substituting equation (40) into equation (39):

$$\alpha = \frac{4\pi k}{\lambda} \tag{41}$$

By applying the known value for $\alpha_{254}$ (calculated α) and solving for K:

$$k = \frac{\alpha_{254} \cdot \lambda_{254}}{4\pi} \tag{42}$$

Now the absorption coefficients for the upper wavelengths (such as at about 400 nm) and for the lower wavelengths (such as at about 185 nm) can be calculated.

$$\alpha_{400} = \frac{k \cdot 4\pi}{\lambda_{400}} \tag{43}$$

$$\alpha_{185} = \frac{k \cdot 4\pi}{\lambda_{185}} \tag{44}$$

By calculating this "expanded" information, a better determination can be made as to exactly what photonic energy is being dosed.

By way of example only, in situations where no additional chemical or other oxidant is being used, those wavelengths below about 254 nm will be important. Principally, wavelengths at or about 185 nm will cause photolysis into water yielding [·OH] free radicals.

As another example, at or about 220 nm ozone is produced from dissolved oxygen ($O_2+O_2 \rightarrow O_3 +O$). The O is very reactive and plays a part in the atomic abstraction of organic contaminants. Therefore, if these wavelengths are being attenuated because of high total dissolved solids, then the flow rate can be lowered so as to allow for a higher dosage rate. Thus, dosage is proportional to intensity and time, or to lamp power, or to pulse repetition rate. Furthermore, if these wavelengths are being attenuated because of normal or abnormal lamp aging, then flow rate can be lowered to an acceptable limit. In the cases where an adjunct chemical or other oxidant is used, the higher energy, shorter wavelengths are also important. The oxidant can often or usually be stimulated at longer wavelengths which are not so easily absorbed by the total dissolved solids. Therefore, oxidation can occur at higher flow rates.

In step 11, actual calculation of the opacity of the water matrix at the selected wavelengths can be made:

$$I=I_o e^{-\alpha \Delta Z} \approx CH1 \cdot e^{-\alpha \Delta Z} \qquad (45)$$

In step 12, a determination is made as to whether or not transmission is below a threshold setpoint, or not. This determination is made based upon measured opacity. If a low transmission is determined, proceed to step 13. If not, the preset, predetermined or otherwise previously adjusted flow rate, flashlamp power and oxidant infusion rates are maintained. Optionally, the counter can be reset at this point to a value of 1 and the measuring cycle repeated. If not, proceed to step 14. In step 13, therefore, flow rate, flashlamp power and oxidant infusion rates are readjusted to approach and hopefully achieve the optimum dosage, and step 14 is an optional operator or system interrupt in the measuring cycle.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. A method for photolytic decontamination of water utilizing deep UV-peaked near blackbody radiation, the water having one or more oxidizing components of contaminants, the method utilizing a reactor comprising a reaction chamber with an internal space, an inlet and an outlet and at least one flashlamp type broadband radiator which generates pulses of deep UV-peaked radiant energy at a rate of between about 1 and about 500 pulses per second with wavelengths between about 150 nm and about 3 $\mu$m at between about 1 KW and about 15 MW peak power, the reactor further comprising at least a near optical sensor system for determining the energy level of radiation near the flashlamp and a far optical sensor system for determining the energy level of radiation at a point in the water farther away from the flashlamp, the method comprising the following steps:

(A) Sustaining a free radical chain reaction of the oxidizing components of contaminants in the water by providing a dosage rate of broadband radiation between about 1 joule/cm$^2$ and about 5000 joules/cm$^2$;

(B) Determining the attenuation of radiant energy through the water at a given wavelength by measuring the energy at the given wavelength with the near and the far optical sensor systems; and (C) Adjusting the dosage rate of broadband radiation based upon the determined attenuation of energy at the given wavelength through the water.

2. The method of claim 1, further comprising the following steps:

(D) Determining the attenuation of radiant energy through the water at additional wavelengths based upon the degree of attenuation of the radiant energy at the given wavelength as determined in step (B); and (E) Adjusting the dosage rate of broadband radiation based upon the determined attenuation of energy at the additional wavelengths through the water.

3. A differential photo-feedback analysis method for controlling photolytic decontamination of water utilizing deep UV-peaked near blackbody radiation, the water having one or more oxidizing components of contaminants, the method utilizing a reactor comprising a reaction chamber with an internal space, an inlet and an outlet and at least one flashlamp type broadband radiator which generates pulses of deep UV-peaked radiant energy at a rate of between about 1 and about 500 pulses per second with wavelengths between about 150 nm and about 3 $\mu$m at between about 1 KW and about 15 MW peak power, the reactor further comprising at least a near optical sensor system for determining the energy level of radiation near the flashlamp and a far optical sensor system for determining the energy level of radiation at a point in the water farther away from the flashlamp, the control method comprising the following steps:

(A) Initiating a free radical chain reaction of the oxidizing components of contaminants in the water by providing a dosage rate of broadband radiation between about 1 joule/cm$^2$ and about 5000 joules/cm$^2$;

(B) Determining the coefficient of absorption of radiant energy through the water at a given wavelength by measuring the energy at the given wavelength with the near and the far optical sensor systems;

(C) Adjusting the dosage rate of broadband radiation based upon the coefficient of absorption at the given wavelength through the water.

4. The method of claim 3 in which the step of adjusting the dosage rate is performed by adjusting the flow rate of water through the reactor.

5. The method of claim 3 in which the step of adjusting the dosage rate is performed by adjusting the power input to the flashlamp.

6. The method of claim 3 in which the step of adjusting the dosage rate is at least partially replaced by a step of adjusting the rate of infusion of chemical oxidant.

7. The method of claim 3, further comprising the following steps:

(D) Calculating the coefficient of absorption of radiant energy through the water at additional wavelengths based upon the degree of attenuation of the radiant energy at the given wavelength as determined in step (B);

(E) Adjusting the dosage rate of broadband radiation based upon the calculated coefficient of absorption at additional wavelengths.

* * * * *